(12) United States Patent
Almog et al.

(10) Patent No.: US 6,340,346 B1
(45) Date of Patent: Jan. 22, 2002

(54) METHOD AND SYSTEM FOR SYSTEM IDENTIFICATION OF PHYSIOLOGICAL SYSTEMS

(75) Inventors: Yael Almog, Rosh Haiyin; Eran Toledo, Tel Aviv, both of (IL)

(73) Assignee: T.A.O. Medical Technologies Ltd., Herzliya (IL)

( * ) Notice: Subject to any disclaimer, the term of this patent is extended or adjusted under 35 U.S.C. 154(b) by 0 days.

(21) Appl. No.: 09/449,752

(22) Filed: Nov. 26, 1999

(51) Int. Cl.$^7$ .................................................. A61B 5/00
(52) U.S. Cl. ........................ 600/300; 128/898; 600/301
(58) Field of Search ................................. 600/300, 301, 600/304, 313, 338, 351, 376, 511, 481, 529; 128/898

(56) References Cited

U.S. PATENT DOCUMENTS

| | | |
|---|---|---|
| 4,821,732 A | 4/1989 | Lippes |
| 5,123,420 A | 6/1992 | Paret |
| 5,425,362 A | 6/1995 | Siker et al. |
| 5,433,204 A | 7/1995 | Olson |
| 5,442,940 A | 8/1995 | Secker et al. |
| 5,474,065 A | 12/1995 | Meathrel et al. |
| 5,596,993 A | 1/1997 | Oriol et al. |
| 5,623,939 A | 4/1997 | Garfield |

OTHER PUBLICATIONS

Loyke, HF, "Cold Pressor Test as a Predictor of the Severity of Hypertension", South–Med–J., 88(3):300–304, 1995 (abstract).

Chang et al., "The Analysis of Relationship Between Fetal Stress and Blood Dynamics in Fetal Vessals", Chung–Hua–Fu–Chan–Ko–Tsa–Chih, 31(1):15–7, Jan. 1996, (abstract).

Chon et al., "Linear and Nonlinear System Identification of Autonomic Heart–Rate Modulation", IEEE Engineering in Medicine and Biology, pp 96–104, 1997.

North et al, "Uterine Artery Doppler Flow Velocity Waveforms in the Second Trimester for the Prediction and Fetal Growth Retardation", Obstetrics & Gynecology, 83(3):378–386, 1994.

Gudson et al, "A Clinical Evaluation of the "Roll–Over Test" for Pregnancy–Induced Hypertension" Am, J. Obstet. & Gynecol, 127(1):1–3, 1977.

Eneroth–Grimfors et al., "Evaluation of Three Simple Physiologic Tests as Predictors of Pregnancy–Induced Hypertension", Acta Obstet Gynecol Scand, 67:109–113, 1988.

Peck TM, "A Simple Test for Predicting Pregnancy–Induced Hypertension", Obstetrics & Gynecology, 50(5):615–617, 1977.

(List continued on next page.)

*Primary Examiner*—Eric F. Winakur

(57) ABSTRACT

A system for monitoring a pregnancy in a pregnant woman having a maternal-placenta-fetal system is disclosed. The system comprises (a) at least one monitoring device simultaneously monitoring selected maternal and fetal physiological signals; and (b) a computerized system being in communication with each of the at least one monitoring device for preprocessing the maternal and fetal physiological signals by independently non-linearly or linearly mathematically decomposing the maternal and fetal physiological signals into mathematical constituents thereof and collecting constituents of the mathematical constituents having a highest degree of linearity and/or simplicity, and for using the constituents having the highest degree of linearity and/or simplicity for identifying a mathematical model describing the maternal-placenta-fetal system, and mathematical parameters describing the model.

27 Claims, 15 Drawing Sheets

OTHER PUBLICATIONS

Anderson, GJ, "The Roll–Over Test as a Screening Procedure for Gestational Hypertension", Aust. & N.Z. J, of Obstet and Gyn. 20:144–146, 1980.

Baker et al., "The Use of the Hand–Grip Test for Predicting Pregnancy–Induced Hypertension", Europ. J. of Obstet & Gynecol & Repro. Biol., 56:169–172, 1994.

Degani et al, "Isometric Exercise Test for Predicting Gestational Hypertension", Obstetrics & Gynecology, 65(5):65–654, 1985.

Fairlie, Fmc, "Doppler Flow Velocimetry in Hypertension in Pregnancy", Clinics in Perinatology, 184(4):749–777, 1991.

Badalian, SS, "Nature and Mechanism of Hemodynamic Changes in Fetuses of Mothers with Various Types of Diabetes Mellitus", Akush–Ginekol–Mosk, 1989. Sep. (9):39–42 (Abstract).

Jung L, "Sytem Identification: Theory for the User", Prentice–Hall, Englewood Cliffs, N.J. Ed. T. Kon Lath, 1987, Chap 1, pp 69–89.

Weiner, N., "Nonlinear Problems in Random Theory", New York, Wiley, 1985 pp 1–15.

Marmarelis, VZ, "Identification of Nonlinear Biological Systems Using Laguerre Expansions of Kernels", Annals of Biomedical Engineering, 21:573–589, 1993.

Lee et al, "Measurement of the Weiner Kernels of a Non-Linear System by Cross–Correlation", Int. J. Control, 2:237–254, 1965.

Sibai, BM, "Diagnosis and Management of hronic Hypertension in Pregnancy", Obstetrics & Gynecology, 78(3):451–461, 1991.

Nylund et al., "Uteroplacental Blood Flow in Diabetic Pregnancy: Measurements with indium 113m and a computer–linked gamma camera", Am. J. Obstet. Gynecol, 144:298–302, 1982.

Branch et al., "Obstetric Complications Associated with the Lupus Anticoagulant", New England J. of Medicine, 313:1322–1325, 1985.-

Pre-processing procedure

- Evaluate the data
- Synchronize the various signals obtained from maternal origin as well as fetal origin
- Filter the data
- Decimate the data to the optimal sampling rate chosen for that specific signal
- Divide the data into non overlapping segments

Fig. 5

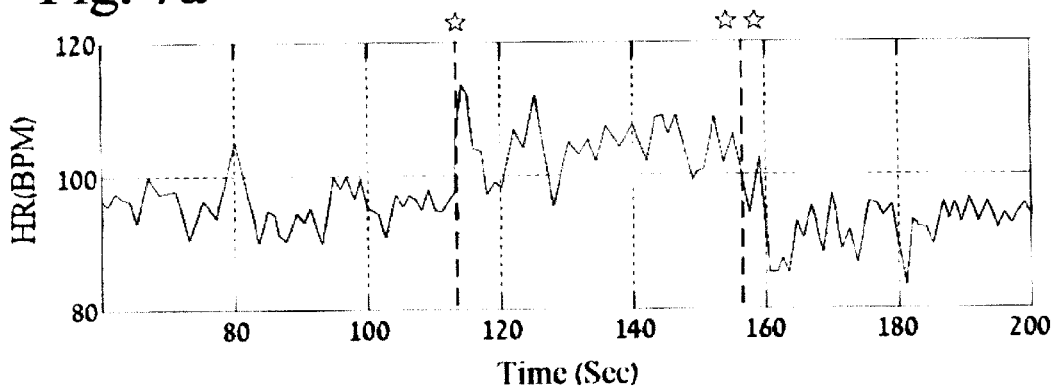
Fig. 7a  Maternal Heart Rate
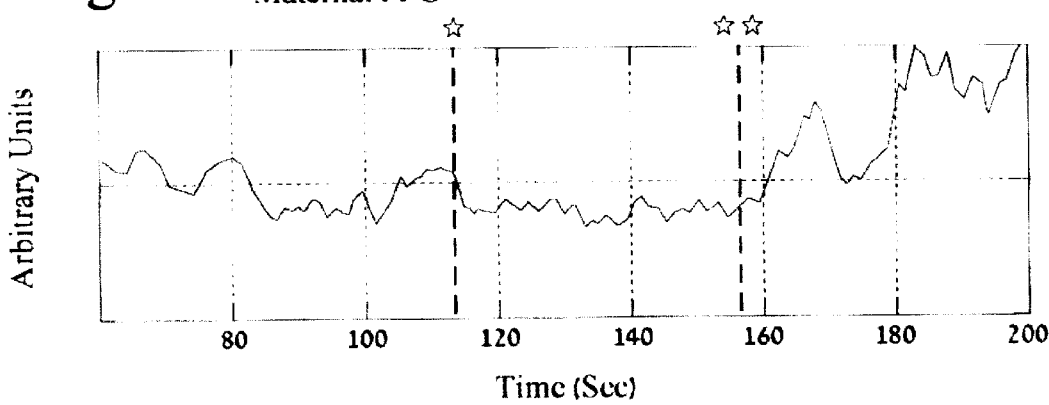
Fig. 7b  Maternal PPG
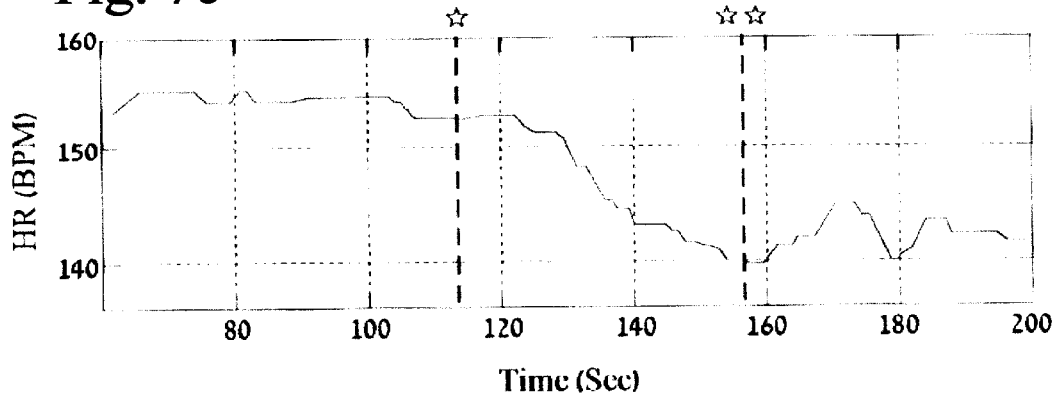
Fig. 7c  Fetal Heart Rate
☆   Beginning of External Manipulation
☆☆  End of External Manipulation

Fig. 8a  Maternal Heart Rate
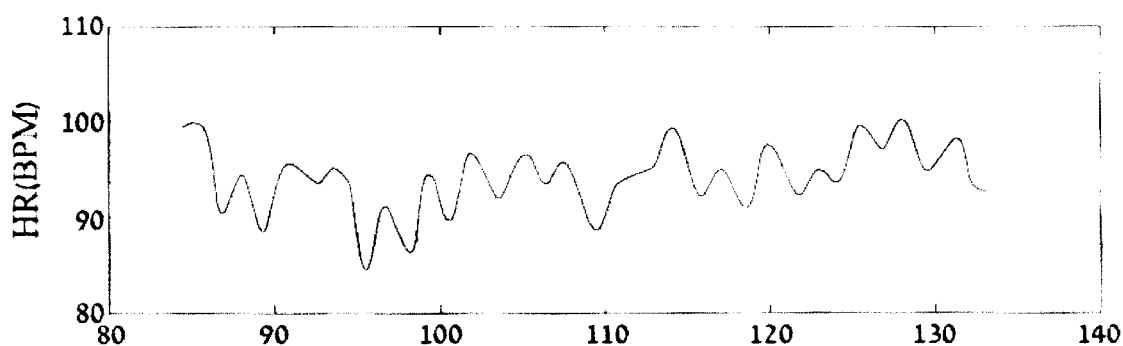
Fig. 8b  Maternal PPG
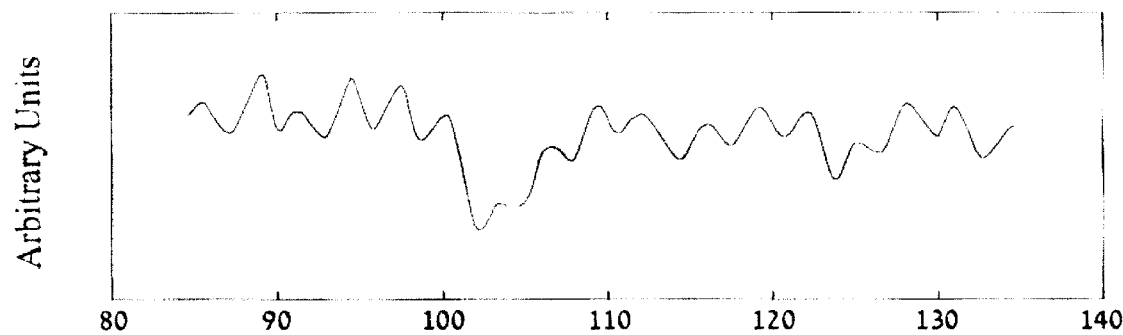
Fig. 8c  Fetal Heart Rate
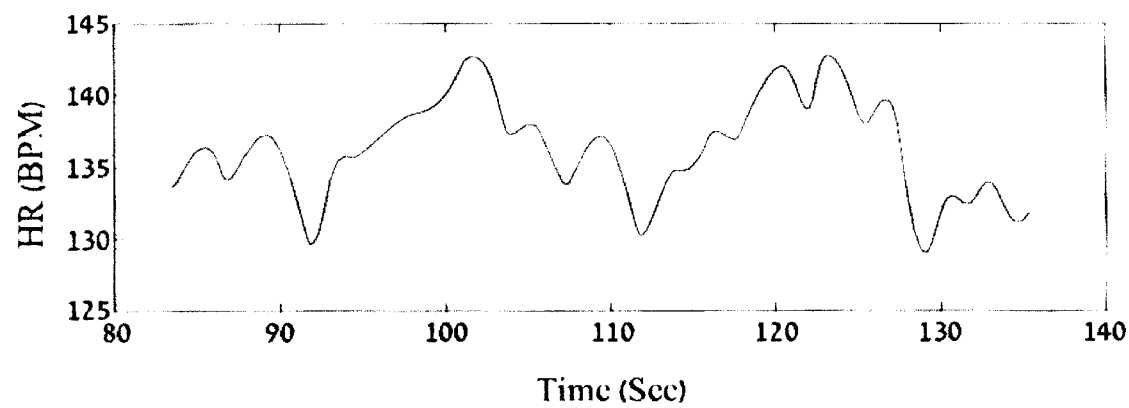

Fig. 8d  Box-Jenkins model $$y(t) = \frac{B_1(q)}{F_1(q)} u_1(t-nk) + \frac{B_2(q)}{F_2(q)} u_2(t-nk) + \frac{C(q)}{D(q)} e(t)$$

y(t) - Output Signal (Fetal Heart Rate).
$u_1(t)$ - First Input Sgnal (Maternal Heart Rate).
$u_2(t)$ - Second Input Signal (Maternal PPG).
e(t) - Noise.
$B_1(q)$, $F_1(q)$, $B_2(q)$, $F_2(q)$, $C(q)$, $D(q)$ - Polynoms in Fig. 8e  Parameters of the Model fitted to the Data $B_1(q) = -3.198 \cdot 10^{-3} q + 0.3323 \cdot 10^{-3}$
$B_2(q) = -4.753 \cdot 10^{-5} q + 4.821 \cdot 10^{-5}$
$F_1(q) = q^2 - 1.947 q + 0.980$
$F_2(q) = q^2 - 1.995 q + 0.996$
$C(q) = q^2 + 0.0052 q - 0.165$
$D(q) = q^2 - 1.937 q + 0.946$ Fig. 8f  Fetal Heart Rate, measured and simulated

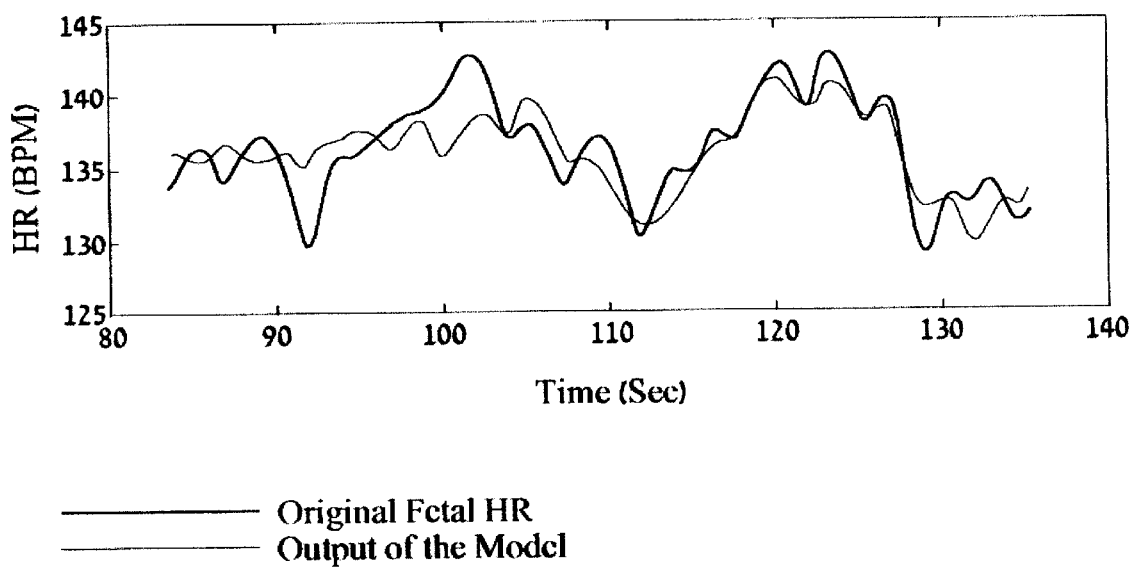

———— Original Fetal HR
———— Output of the Model

METHOD AND SYSTEM FOR SYSTEM IDENTIFICATION OF PHYSIOLOGICAL SYSTEMS

RELATED PATENT APPLICATIONS

This application is related to PCT/US99/18060 filed Aug. 9, 1999 which claims priority from U.S. Pat. No. 09/140,889 filed Aug. 27, 1998.

FIELD AND BACKGROUND OF THE INVENTION

The present invention relates to a method and system for simplification of the relation between two physiological systems and, more particularly, to simplification of the relation between two physiological systems using system identification techniques.

Physiological Background

It has become a common practice in obstetrics to evaluate the well being of the fetus in utero. This practice, which is known as antepartum testing, has been extensively practiced since the early 1970 on certain high risk obstetrical patients. One of the uses of antepartum testing is to determine how well the placenta is supplying the oxygen and nutrient needs of the growing fetus, and removing fetal wastes therefrom.

Almost 70% of fetal deaths occur before the onset of labor. Antepartum fetal death accounts for nearly 40% of all prenatal mortality in the United States. The majority of fetal deaths occur before 32 week's gestation.

Antepartum fetal deaths may be categorized into four broad categories: (i) chronic asphyxia of diverse origin; (ii) congenital malformations; (iii) superimposed complications of pregnancy, such as Rhesus isoimmunization, placental abruption, hypertension, diabetes and fetal infection; and (iv) deaths of unexplained cause.

Based on available data, approximately 30% of antepartum fetal deaths may be attributed to asphyxia, 30% to maternal complications, especially placenta abruption, hypertension, and preeclapmsia, 15% to congenital malformations and chromosomal abnormalities, and 5% to infection.

The clinical experience has demonstrated that antepartum fetal assessment can have a significant impact on the frequency and cause of fetal deaths.

Indications for antepartum fetal monitoring in patients known to be at risk of utero-placental insufficiency include maternal, fetal, placental and background indications. Maternal indications include prolonged pregnancy; diabetes mellitus; hypertension and advanced maternal age. Fetal indications include: suspected intrauterine growth restriction (IUGR) and decreased fetal movements. Placental indications include: abruption of the placenta and abnormal amniotic fluid. Background indications include: previous stillbirth.

The fetus and the placenta well being depend upon unique physiological systems responsible at providing an environment capable of supporting fetal growth and development.

To appreciate the complexity of the placenta as a bidirectional transfer organ, it is necessary to point out that the placenta provides the fetus with products which are essential for its well being including essential nutrients, fluids and oxygen, and it serves as a route for clearance of fetal excretory products [Williams Obstetrics, Pritchard and Mc Donald eds., Appleton-Century-Crofts, New York, 1980].

The transport characteristics of the placenta allow respiratory gases and many solutes to reach equal concentration between the maternal intervillous space blood and fetal capillary blood. Thus, the rate of blood flow in these two circulations is important in the determination of fetal oxygen and nutrient supply. Over the course of a normal singleton gestation, uterine blood flow increases more than 50-fold above non-pregnant values. Two factors contribute to this dramatic increase in blood flow: placental growth and maternal arterial vasodilatation.

The uterine artery behaves as a nearly maximally dilated system. Fetal blood flow to the umbilical circulation represents approximately 40% of the fetal cardiac output. During the first trimester, increase in umbilical blood flow is directly proportional to fetal growth.

Many maternal organs undergo physiological changes during the course of pregnancy. Maternal cardiac output, i.e., the product of heart rate and stroke volume, increases by about 30–50% during pregnancy. The distribution of maternal cardiac output changes as pregnancy progresses. In the first trimester the uterus receives about 3% of the cardiac output, however it receives about 17% of the cardiac output near term.

The percentage of cardiac output devoted to kidney, brain and skin is not dramatically altered by pregnancy. Peripheral vascular resistance falls during pregnancy. The cause for this is the smooth muscle relaxing effect of high progesterone levels associated with the pregnancy. There is a progressive rise in venous pressure in the lower extremities.

The placenta, the mother and the fetus make important contribution to the immunological maintenance of pregnancy.

Advances in prenatal and neonatal health care have resulted in a substantial reduction in prenatal and neonatal mortality. These improvements primarily relate to better capabilities in treating maternal diseases during pregnancy, advance in neonatal care and may also be due to improvements in antepartum fetal surveillance techniques.

There are some medical conditions in pregnancy that may lead to poor placental functioning such as diabetes, hypertension, anemia and prolonged pregnancy. In these conditions it is of great importance to evaluate placental functioning. For these or other indications obstetrician will determine whether one is in need to have antepartum testing during the pregnancy.

Antepartum fetal testing is a term that embraces data from fetal movement counts to biophysical monitoring methods, such as contraction stress test, nonstress test, fetal biophysical monitoring profile, amniotic fluid assessment, Doppler velocimetry, vibro-acoustic fetal stimulation and computerized fetal heart rate.

The following lists few of the tests used for fetal monitoring.

Antepartum Fetal Heart Rate Testing (non stress test, NST)

In NST, fetal heart rate acceleration in response to fetal movement are recorded via electronic equipment on a strip of paper.

Cardiotocography (CTG)

CTG utilizes electronic equipment to record the fetus' heart rate pattern. Uterine contractions, if present, are also registered. This information is recorded on a strip of paper, producing a tracing that is read by the obstetrician. Certain changes in the fetal heart rate pattern can signal a problem.

Amniotic Fluid Index (AFI)

The amount of amniotic fluid surrounding the fetus may be decreased in some high-risk pregnancies. The amount of amniotic fluid present is measured by ultrasound scanning and is known as AFI.

Fetal Biophysical Profile (FBP)

The CTG trace is obtained and then four parameters are observed by ultrasound. The four parameters are fetal tone, fetal movements, fetal breathing, and the amniotic fluid index. Not all of these tests need to be performed at the same time.

Since there are many different pathophysiological processes leading to fetal asphyxia, indication-specific testing is reasonable and it may allow early identification of at-risk fetuses. The FBP is useful in the detection of developing fetal asphyxia even before it irreversible affects the fetus.

No program of antepartum fetal testing can completely remove the risk of fetal death. The most appropriate antepartum tests appear to be amniotic fluid volume assessment, fetal tone and fetal heart monitoring.

The use of Doppler ultrasound is not beneficial in most clinical cases. The single most effective test that distinguishes normal-small from compromised small fetuses is the determination of the umbilical artery Doppler waveform.

Doppler velocimetry seems to be reliable in diagnosing conditions predisposing to IUGR such as chronic hypertension, collagen vascular disorders, and other diseases in which vasospasm plays a major role.

Hence, it remains uncertain which is the optimal Doppler ultrasound measurement of the uteroplacental circulation to obtain the best sensitivity and predictive values for evaluation of fetal and placental pathologies such as preeclampsia and IUGR [Northe R. A., Ferrier C, Long D, Townend K and Pinkus-Smith P. Uterine artery and flow velocity waveforms in the second trimester for the prediction of preeclampcia and fetal growth retardation. Obstetrics and Gynecology Vol 83 pp. 378–386, 1994].

The usual decrease in utheroplacental blood flow associated with uterine contraction, when superimposed with chronic utheroplacental insufficiency (e.g., diabetes associated with vascular changes, postdatism) may result in acute fetal distress.

In contrast, maternal hypotension (e.g., after induction of spinal or epidural anesthesia) can cause acute fetal distress despite the presence of a normal utheroplacental unit. Furthermore, maternal positioning has a strong influence on the condition of the fetus.

There are strong indications that the utheroplacental unit has specific characteristics which can be evaluated by a variety of external manipulations [Gusdon J P Jr, Anderson S G, May W J. A clinical evaluation of the "roll-over test" for pregnancy induced hypertension. Am J obstet Gynecol 1: 127(1): 1–3, January 1997; Eneroth-Grimforms E, Bevegard S, Nilsson Ba. Evaluation of three simple physiological tests as predictors of pregnancy-induced hypertension. A pilot study. Acta Obstet Gynecol Scand; 67(2):109–113, 1988; Peck T M A simple test for predicting pregnancy-induced hypertension. Obstet Gynecol 50(5):615–617 November 1977; Andersen G J. The roll over test as a screening procedure for gestational hypertension. Aust N Z J Obstet Gynecol 20(3): 144–150, August 1980; Baker P N, Johnson I R. The use of the hand-grip test for predicting pregnancy—induced hypertension. Eur J Obstet Gynecol Reprod Biol 56(3):169–172, September 1994; Degani S, Abinader E, Eibschitz I, Oettinger M, Shapiro I, Sharf M. Isometric exercise test for predicting gestational hypertension. Obstet Gynecol 65(5):652–654, May 1985; Loyke H F. Cold pressor test as a predictor of the severity of hypertension. Sounth Med J ; 88(3):300–304, May 1995; Chang C, Zhang J. The analysis of relationship between fetal stress and blood dynamics in fetal vessels and placenta bed vessels. Chung Hau Fu Vhan Tsa Chin 31(1)46:15–17, January 1996; Cottrill C M, Jeffers Lo J, Ousey J C, McGladdery A J, Ricketts S W, Silver M, Rossdale PD. The placenta as a determinant of fetal well being in normal and abnormal pregnancies. J. Reproduct Fertil Suppl 44:591–601, 1991; Fairlie F M. Doppler flow velocimetry in hypertension in pregnancy. Clin Perinatol 18(4):749–778, December 1991; Badalian S S. Nature and mechanism of hemodynamic changes in fetuses of mothers with various types of diabetes mellitus. Akush Ginekol Mosk 9:39–42, September 1989.

There is no doubt that better objective and advanced measures of placenta well being and fetal asphyxia and asphyxia-related morbidity are needed to allow for a more scientific approach of antenatal fetal surveillance.

Mathematical Background

Modulation and Demodulation

The modulation process combines a narrowband signal, s(t), with a signal of higher frequency (relative to the frequency band of s(t)). Modulating a high frequency signal (known as the carrier, c(t)) is advantageous since low frequency signals cannot be transmitted through most media. For example, transmitting a speech signal, with frequencies of 300–4000 Hz as a radio signal is highly difficult but after modulating it on a 100 MHz carrier, the task becomes much easier. A second advantage of modulation is the ability, using numerous carriers, to transmit many signals with the same basic frequencies without interference. Demodulation is the complementary process of extracting the narrowband signal, s(t), from the carrier, c(t). A common modulation scheme is the Amplitude Modulation (AM) [Couch L. W. Digital and Analog Communication Systems. 5th ed., 1997 Prenctice-Hall Jew-Jersey]:

$$r(t) = A \cdot (1 + m \cdot s(t)) \sin(2\pi f_c t)$$

where r(t) is the transmitted signal; A is the amplitude of the transmitted signal; m is the modulation index and ranges between 0 and 1; s(t) is the modulating signal containing the information; and $f_c$ is the frequency of the carrier.

A similar modulation scheme is the Double-Sideband Suppressed Carrier (DSB-SC). This modulation resembles an amplitude modulation with suppressed carrier [Couch L. W. Digital and Analog Communication Systems. 5th ed., 1997 Prenctice-Hall Jew-Jersey]:

$$r(t) = A \cdot s(t) \cdot \sin(2\pi f_c t)$$

Usually it is assumed that the modulating signal, s(t), has no DC component.

Another common modulation scheme is the Frequency Modulation (FM) [Couch L. W. Digital and Analog Communication Systems. 5th ed., 1997 Prenctice-Hall Jew-Jersey]:

$$r(t) = A \sin\left(2\pi f_c t + \beta \int_{-\infty}^{t} s(\tau) d\tau\right)$$

where β is the maximal frequency shift.

The instantaneous frequency of the carrier equals a constant plus the modulating signal. A closely related modulation scheme is the Phase Modulation (PM) in which the phase of the carrier is the modulating signal [Couch L. W.

Digital and Analog Communication Systems. 5th ed., 1997 Prenctice-Hall Jew-Jersey]:

$$r(t)=A\sin(2\pi f_c t + \beta s(t))$$

Modulation of information of high frequency carriers can occur from natural processes also. For example, a transmitted ultrasound signal is reflected from a moving tissue with a small frequency shift which is known as the Doppler shift. This shift, which is proportional to the velocity of the reflecting tissue, can be extracted from the incoming ultrasound signal using conventional FM demodulation techniques.

System Identification Techniques

A system is an object in which different kind of variables interact and produce observable signals [Ljung L. *System Identification; theory for the user*. Prentice-Hall Inc., Englwood Cliffs, N.J. Edited by T. Kailath, 1987]. The observable signals that are of interest are usually referred to as "outputs". The system is also affected by external stimuli. External signals that can be manipulated by the observer are referred to as "inputs". Others are referred to as "disturbances" and can be divided into those that are directly measured and those that are only observed through their influence on the output. The distinction between inputs and measured disturbances is often less important for the modeling process.

Clearly, the notion of a system is a broad concept and plays an important role in modern science. Dynamic systems are those for which the current output value depends not only on the current external stimuli but also on earlier values.

When one interacts with a system, one needs to have a concept of how the system's variables relate to one another. With a broad definition, the relationship among observed signals is referred to as "a model of the system". Models can come in various shapes with varying degree of mathematical formalism. The intended use determines the degree of sophistication that is required to make the model purposeful.

Mathematical models describe the relationship among system variables in terms of mathematical expressions like difference or differential equations. Mathematical models may be characterized by a number of adjectives (time continuous or time discrete, lumped or distributed, deterministic or stochastic, linear or nonlinear, etc.) signifying the type of differential equation used.

Basically, a model has to be constructed from observed data. Mathematical models may be developed along two routs.

One route is to split the system into subsystems, whose properties are well understood from previous experience. These subsystems are then joined mathematically and a model of the whole system is obtained. This route is known as "Modeling", and does not necessarily involve any experimentation on the actual system.

The other route to mathematical as well as graphical models is directly based on experimentation. Input and output signals from the system, are recorded and subjected to data analysis in order to infer a model. This route is known as "System Identification", the final outcome of which is a model of the system under study.

System identification is the subject of constructing or selecting models of dynamic systems to serve certain purposes. A first step is to determine a class of models within which the search for the most suitable model is to be conducted. A model of a system is a description of its properties, suitable for a certain purpose. The model need not be a true and accurate description of the system, nor need the user believe it to be so, in order to serve its purpose.

Quiet often it is not possible to determine, apriori, the coefficients characterizing the system from knowledge of the physical mechanisms that govern the system's behavior. Instead, the determination of all or some of them must be left to estimation procedures. The model thus becomes a set of models and it is for the estimation procedure to select that member in the set that appears to be the most suitable for the purpose in question.

The procedure to determine a model of a dynamic system from observed input-output data involves four basic ingredients [Ljung L. System Identification; theory for the user. Prentice-Hall Inc., Englwood Cliffs, New Jersy. Edited by T. Kailath, 1987]:

1. The data: The input-output data which are recorded during a specific designed identification procedure.
2. A set of candidate models: A set of candidate models is obtained by specifying within which collection of models one is going to look for a suitable one.
3. A rule by which candidate models can be assessed using the data: This is the identification method, and is based on the performance of the model when one attempts to reproduce the measured data. A deficient model in these respects makes one reject the model, while good performance will develop a certain confidence in the model.
4. The procedure of identification is repeated for nonoverlapping segments of each set of data, in order to evaluate the accuracy of the model and the confidence level of the results.

However, a model can never be regarded as a final and true description of the system. It can at best be regarded as a good enough description of certain aspects of particular interest.

Several system identification models are known in the art, such as, for example, nonparametric models, parametric models, polynominal representation, simple autoregressive model, ARMAX model structure, output error structure, Box-Jenkins model structure, general parametric model structure, state space representation, linear time-varying models, time-invariant model, nonlinear models, nonlinear ARMAX, Wiener kernels model, Korenberg-Billings model and Volterra-Wiener model.

The present invention is based on the broad concept of system identification, using the relationship between mother and fetus as an input-output open-loop system connected by a connection function. System identification deals with the problem of building mathematical models of dynamic systems, based on observed data. The area has matured into an established collection of basic techniques that are well understood and known to be successfully performed in practical applications. Since the mother and fetus are connecting solely via the placenta, the present invention enables placental and fetal functionality assessment.

There is thus a widely recognized need for, and it would be highly advantageous to have, a method and system for evaluating the condition of the placenta in pregnant women as well as the well being of the fetus by using physiological parameters and system identification methods.

SUMMARY OF THE INVENTION

According to one aspect of the present invention there is provided a method of determining the well being of a placenta in a pregnant woman having a maternal-placenta-fetal system, the method comprising the steps of (a) simultaneously monitoring selected maternal and fetal physiological signals; (b) preprocessing the maternal and fetal physiological signals by independently non-linearly or linearly mathematically decomposing the maternal and fetal physiological signals into mathematical constituents thereof and collecting constituents of the mathematical constituents having a highest degree of linearity and/or simplicity; (c) using the constituents having the highest degree of linearity and/or simplicity for identifying a mathematical model describing the maternal-placenta-fetal system, and mathematical parameters describing the model; and (d) determining, according to the mathematical model and the mathematical parameters describing the mathematical model, the well being of the placenta.

According to another aspect of the present invention there is provided a method of determining the well being of a fetus in a pregnant woman having a maternal-placenta-fetal system, the method comprising the steps of (a) simultaneously monitoring selected maternal and fetal physiological signals; (b) preprocessing the maternal and fetal physiological signals by independently non-linearly or linearly mathematically decomposing the maternal and fetal physiological signals into mathematical constituents thereof and collecting constituents of the mathematical constituents having a highest degree of linearity and/or simplicity; (c) using the constituents having the highest degree of linearity and/or simplicity for identifying a mathematical model describing the maternal-placenta-fetal system, and mathematical parameters describing the model; and (d) determining, according to the mathematical model and the mathematical parameters describing the mathematical model, the well being of the fetus.

According to yet another aspect of the present invention there is provided a method of determining a maternal-fetus relation in a pregnant woman having a maternal-placenta-fetal system, the method comprising the steps of (a) simultaneously monitoring selected maternal and fetal physiological signals; (b) preprocessing the maternal and fetal physiological signals by independently non-linearly or linearly mathematically decomposing the maternal and fetal physiological signals into mathematical constituents thereof and collecting constituents of the mathematical constituents having a highest degree of linearity and/or simplicity; (c) using the constituents having the highest degree of linearity and/or simplicity for identifying a mathematical model describing the maternal-placenta-fetal system, and mathematical parameters describing the model; and (d) determining, according to the mathematical model and the mathematical parameters describing the mathematical model, the maternal-fetus relation.

According to still another aspect of the present invention there is provided a system for monitoring a pregnancy in a pregnant woman having a maternal-placenta-fetal system, the system comprising (a) at least one monitoring device simultaneously monitoring selected maternal and fetal physiological signals; and (b) a computerized system being in communication with each of the at least one monitoring device for preprocessing the maternal and fetal physiological signals by independently non-linearly or linearly mathematically decomposing the maternal and fetal physiological signals into mathematical constituents thereof and collecting constituents of the mathematical constituents having a highest degree of linearity and/or simplicity, and for using the constituents having the highest degree of linearity and/or simplicity for identifying a mathematical model describing the maternal-placenta-fetal system, and mathematical parameters describing the model.

According to further features in preferred embodiments of the invention described below, while simultaneously monitoring the selected maternal and fetal physiological signals the pregnant woman is provoked by an external stimulus.

According to still further features in the described preferred embodiments the physiological signals are selected from the group consisting of ECG, BP, $PO_2$, $PCO_2$, blood flow, blood velocity, blood volume, thermal index and respiration.

According to still further features in the described preferred embodiments the mathematical model is selected from the group consisting of nonparametric models, parametric models, polynominal representation, simple autoregressive model, ARMAX model structure, output error structure, Box-Jenkins model structure, general parametric model structure, state space representation, linear time-varying models, time-invariant model, nonlinear models, nonlinear ARMAX, Wiener kernels model, Korenberg-Billings model and Volterra-Wiener model.

According to still further features in the described preferred embodiments the step of identifying the mathematical model is effected by identifying a best mathematical model describing the maternal-placenta-fetal system, the best mathematical model is selected out of a plurality of available mathematical models and according to predetermined criteria.

According to still further features in the described preferred embodiments the model is a linear model.

According to still further features in the described preferred embodiments the step of preprocessing the maternal and fetal physiological signals includes at least one process selected from the group consisting of (i) calculating a maternal heart rate from an inter-beat interval of maternal ECG; (ii) calculating maternal heart rate from maxima values of maternal blood flow; (iii) calculating a maternal pulse wave velocity from a delay between R-waves of an ECG and corresponding systoles of blood flow signal; (iv) calculating maternal contractility from maternal blood flow by determining maximal derivative in a maternal systole stage; (v) calculating a fetal heart rate from an inter-beat interval of fetal ECG; (vi) calculating a fetal heart rate from an inter-beat interval of fetal Doppler signal representing fetal heart valve closing; (vii) calculating a fetal blood flow using ultrasound reflection from a fetal blood vessel; (viii) calculating a fetal heart rate from fetal blood flow rate; and (ix) calculating a fetal blood flow rate using ultrasound reflection from a fetal blood vessel.

The present invention successfully addresses the shortcomings of the presently known configurations by providing a method and system for evaluating the condition of the placenta in pregnant women as well as the well being of the fetus by using physiological parameters and system identification methods.

Implementation of the method and system for evaluating the condition of the placenta in pregnant women as well as the well being of the fetus by using physiological parameters and system identification methods involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 5 describes the preprocessing steps.

FIGS. 7a–7c are an example of external manipulation, wherein a provocative test, hand grip, is performed for a period of 40 sec in a pregnant woman of 26 weeks gestation age.

FIGS. 8a–8f are an example of model determination for steady state conditions.

DESCRIPTION OF THE PREFERRED EMBODIMENTS

Figure 1:
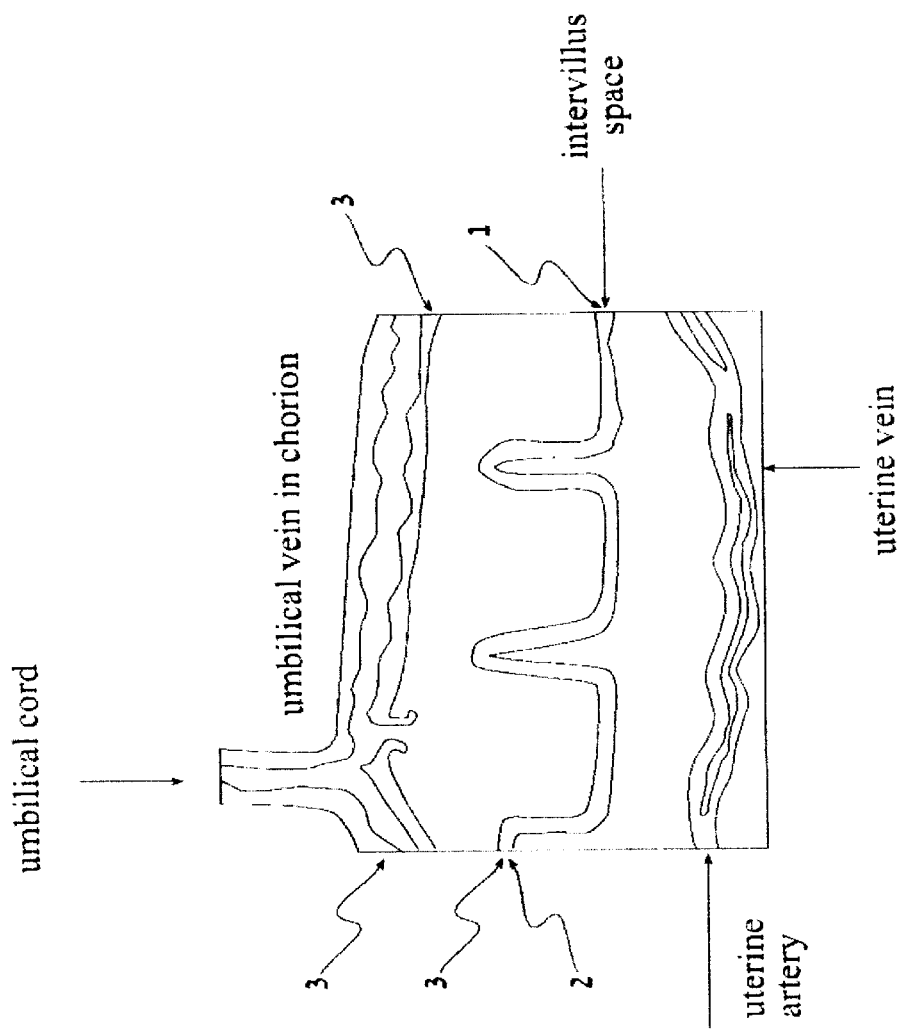
FIG. 1 is a schematic diagram of the maternal-placental-fetal circulation unit.

The present invention is of a method and system for evaluating a pregnant women which can be used for evaluating the condition of the placenta, as well as the well being of the fetus by using physiological parameters and system identification methods. Specifically, the present invention can be used to detect pathologies associated with placental functioning long before a measurable pathology is detectable in the mother or fetus.

The principles and operation of a method and system according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

According to a broad aspect of the present invention, there is provided a method of evaluating the placental-fetal-maternal conditions in pregnant women. The evaluation is performed according to the following steps.

First, selected maternal and fetal physiological signals are simultaneously monitored.

Second, the maternal and fetal physiological signals are independently processed by non-linearly or linearly mathematically decomposing the maternal and fetal physiological signals into mathematical constituents thereof and collecting constituents of the mathematical constituents having a highest degree of linearity and/or simplicity.

Third, a model describing the maternal-placenta-fetal system and parameters describing the model are identified. The model and its parameters collectively define a connection function connecting the input (e.g., measured maternal physiological signals) and the output (e.g., simultaneously measured fetus physiological signals) or in other words describing the maternal-placenta-fetal system.

Fourth, according to the model and the parameters describing the model, the placental-fetal-maternal conditions are evaluated, e.g., as normal or abnormal (e.g., pathological).

Preferably the input is chosen as the maternal signals and the output as the fetus signals. However, the method can also be performed when changing the roles of the input-output, giving parameters which is have no physiological meaning.

It will thus be appreciated that the present invention is based on the broad concept of system identification, using the relationship between the mother and the fetus as an input-output open-loop system connected by a connection function.

As is strongly evident from the literature cited in the Background section, there is a strong correlation between maternal and fetus parameters in various pathophysiological conditions. It is therefore clearly anticipated and it is further shown hereinunder that the mother-placenta-fetus behave as a dynamic system.

System identification deals with the problem of building mathematical models of dynamic systems, based on observed data. The area has matured into an established collection of basic techniques that are well understood and known to be successfully performed in practical applications. The identification of models from data involves decision making while searching for a suitable model. One needs to go through several iterations along the process of arriving to a final model, where at each step previous decisions are revised. There are various techniques for system identification problems ranging from simple linear models to is linear models with noise and more complicated nonlinear models, some of which are described in greater detail hereinunder.

Referring now to the drawings, FIG. 1 shows a schematic diagram of the maternal-placental-fetal circulation units. Maternal blood flows in the uterine blood circuit close to exchange surface 1, whereas fetal blood flows in the placental blood circuit close to exchange surface 1, such that maternal nutrients and oxygen present in the maternal blood cross the intervillous space 2 into the capillaries of the chorionic villi 3, whereas fetal waste products cross space 2 into the maternal blood.

Figure 2:
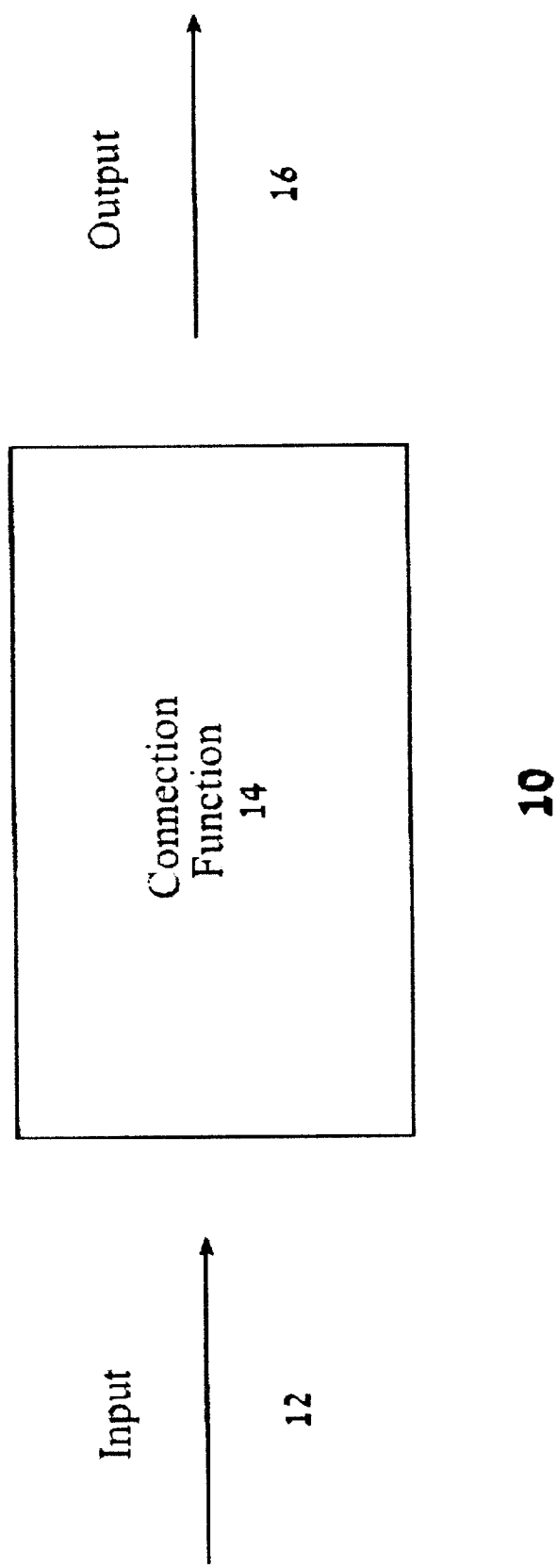
FIG. 2 is a block diagram of the basic concept in accordance with the teachings of the present invention.

FIG. 2 is a basic block diagram of a dynamic system 10 according to the present invention describing a maternal-placenta-fetus system. System 10 features maternal input or inputs 12, a connection function 14 (i.e., model and model parameters), and fetus output or outputs 16. Connection function 14 is selected to best connect between input or inputs 12 and output or outputs 16.

Figure 3:
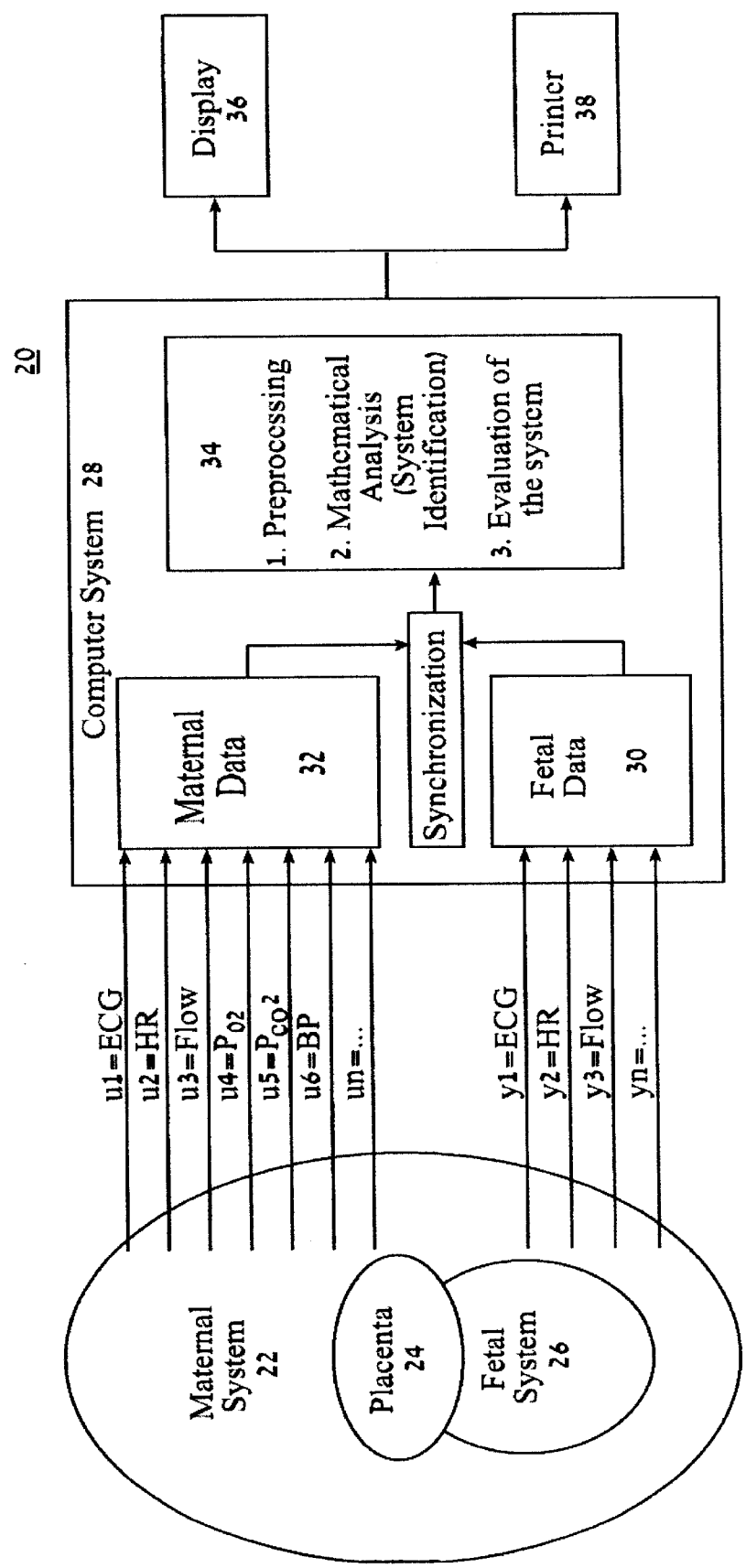
FIG. 3 is a block diagram of an exemplary system for analyzing signals of the maternal-fetal dynamic system according to the present invention.

FIG. 3 is a block diagram of an exemplary system 20 in accordance with the teachings of the present invention. The present invention may be used to evaluate a placenta 24, which is the connecting organ between the mother and the fetus, using signals derived from the maternal system 22, and the fetal system 26.

Maternal physiological parameters, un, such as ECG, BP, $PO_2$, $PCO_2$, blood flow, blood velocity and blood volume, etc., and fetal physiological parameters yn, such as ECG, $PO_2$, $PCO_2$, blood flow, blood velocity and blood volume, etc., are simultaneously recorded using maternal 32 and fetus 30 suitable sensors or devices. If the pregnancy is of more than a single fetus (e.g., twins) separate monitoring may be performed for each of the fetuses by dedicated sensors.

Recordings of the physiological parameters may be effected by sensors or devices known in the art, such as, but not limited to, ultra-sound imaging devices, MRI, electro-magnetic sensors and sound wave sensors. Others include those disclosed in, for example, U.S. Pat. Nos. 4,945,917; 5,596,993; 5,474,065; 5,442,940; 5,623,939; and 5,123,420, which are incorporated by reference as if fully set forth herein.

As a first step following data acquisition, preprocessing of the data is performed. To this end, a computer system 28 is provided and via an analog to digital converter (A/D) (when an analog signal is acquired) it creates discrete time series out of the various physiological parameter recordings. These signals can be maternal heart rate—HR, Systolic blood pressure—S, diastolic blood pressure—D, resistance index—RI, pulsatility index—PI, and others such as S to D ratio.

The various signals, from maternal origin and fetal origin are then synchronized and filtered in order to remove trends and experimental noise.

Physiological parameters of the fetus may also be detected using maternal sensors, for example the determination of fetal HR from maternal ECG, see U.S. Pat. No. 4,945,917.

Computer system 28 then performs an iterative process to choose an optimal connection function 34. The characteristics of connection function 34, as well as the optimal connection function type are evaluated.

The maternal-placenta-fetal systems 22, 24, 26 are described with the most adequate model parameters found. The results of the various estimations and characterizations of systems 22, 24, and 26 are then displayed using a display 36 or a printer 38.

The determined characteristics displayed or printed may be a number, numbers or a plot representative of the determined characteristics. These displays, plots, or numbers may be used by the physician for diagnosis.

Figure 4:
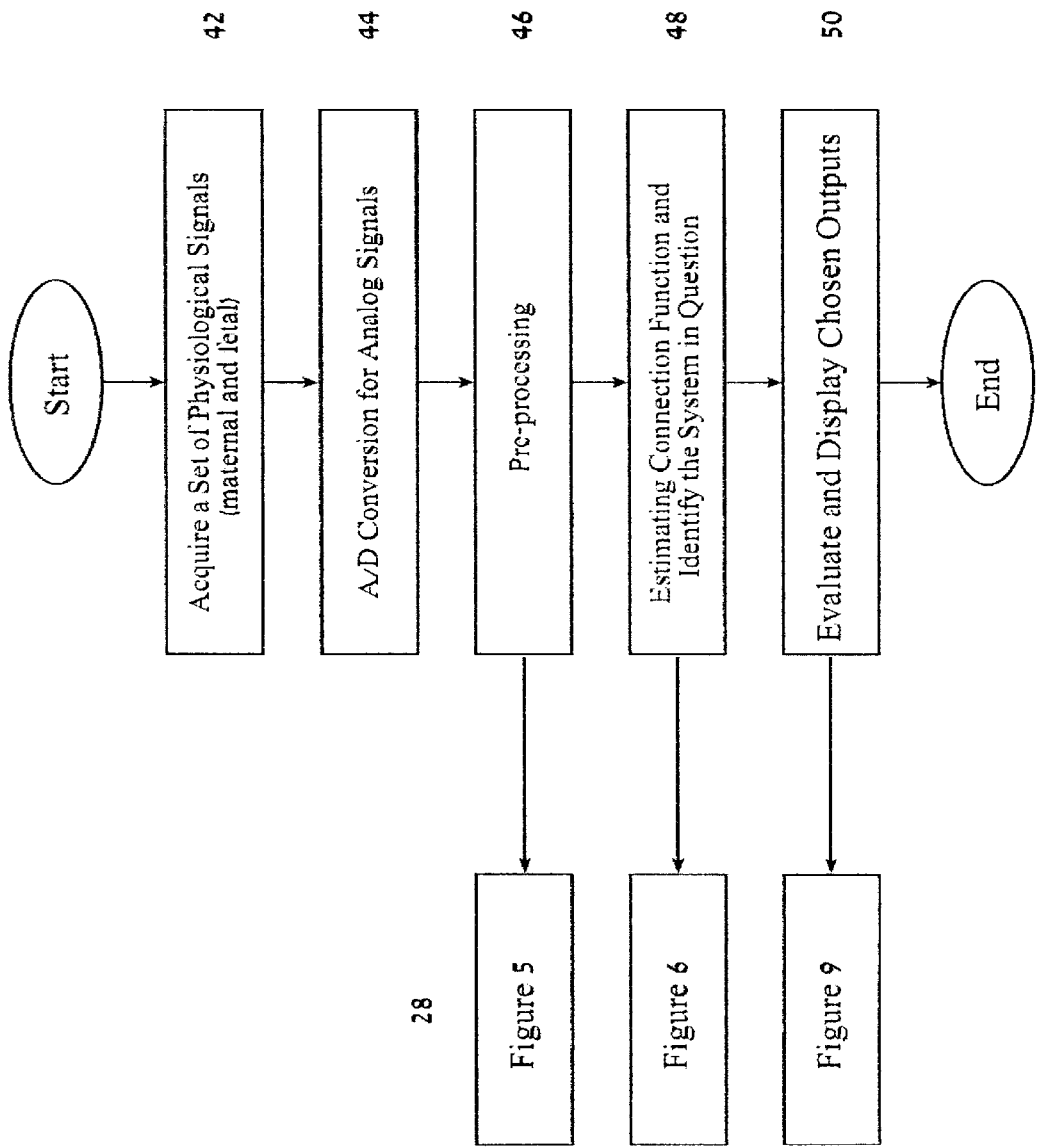
FIG. 4 is a flow diagram of a preferred embodiment of a method of analyzing signals from maternal/fetus system in accordance with the present invention.

Shown in FIG. 4, is a more detailed flow diagram describing the functionality of computer system 28. The first step 42, involves the acquisition of the physiological signals simultaneously taken from both the mother and the fetus. Then, at step 44, A/D conversion is performed for further computer analysis. Shown in step 46 (see also FIG. 5) are the preprocessing steps to prepare the input and output data. In step 48, an iterative computation is executed, using system identification techniques, at the end of which an adequate description of the dynamic system is obtained. In step 50 the outputs are evaluated and optionally displayed. Further description of this step is provided hereinunder with reference to FIG. 9.

Figure 6:
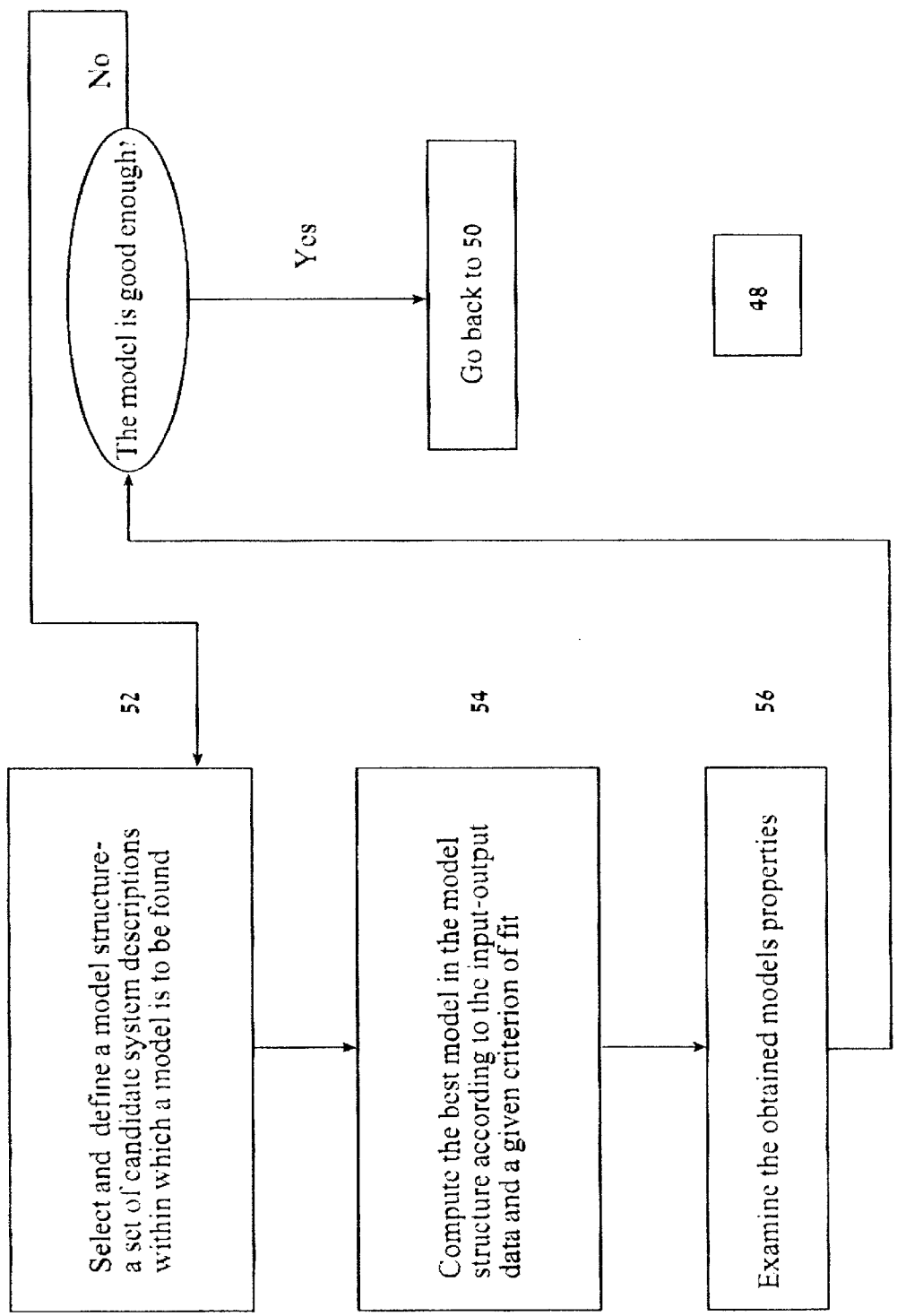
FIG. 6 is a flow diagram of the mathematical procedure performed in the identification process.

A detailed description of step 48 is presented in FIG. 6. There are various potential models to be used under step 52, a description of few is given hereinbelow:

I. Linear time-invariant System Identification a. Nonparametric Models

For experimental data, the aim is to determine a set of functions by direct techniques without first selecting a confined set of possible models. Such methods are called nonparametric since they do not explicitly employ a finite-dimensional parameter vector in the search for the best description.

The nonparametric methods for describing linear models are composed of time-domain methods and frequency-domain methods of various degrees of sophistication.

Assuming that the input-output signals are related by a linear system, the relationship can be written:

$$y(t)=G(q)u(t)+\epsilon(t) \tag{1}$$

where:

u(t): t=1,2, . . . N is the input.

y(t): t=1,2, . . . N is the output.

q is the shift operator and $$G(q)u(t) = \sum_{k=1}^{\infty} g(k)u(t-k) \quad \text{and} \tag{2}$$

$$G(q) = \sum_{k=1}^{\infty} g(k)q^{-k}; \quad q^{-1}u(t) = u(t-1) \tag{3}$$

The numbers {g(k)} are called the impulse response of the system. g(k) is the output of the system at time k if the input is a single pulse at time zero.

The function G(q) is called the transfer function of the system.

When evaluated on the unit circle ($q=e^{iw}$) gives the frequency function:

$$G(e^{iw}) \qquad (4)$$

In Eq. 1 $\epsilon(t)$ is an additional unmeasurable disturbance, noise. Its properties can be expressed in terms of its auto spectrum:

$$\phi_v(\omega) = \sum_{\tau=-\infty}^{\infty} R_v(\tau) e^{-i\omega\tau} \qquad 5.$$

where $R_v(\tau)$ is the covariance function of $\epsilon(t)$. The disturbance $\epsilon(t)$ can also be described as filtered white noise:

$$\epsilon(t)=H(q)e(t) \qquad (6)$$

where $e(t)$ is white noise with variance $\lambda$ and $$\phi_v(\omega)=\lambda|H(e^{i\omega})|^2 \qquad (7)$$

Eqs. 1 and 6 give a time domain description of the system, $$y(t)=G(q)u(t)+H(q)e(t) \qquad (8)$$

Eqs. 4 and 7 constitute a frequency domain description.

Both descriptions are called nonparametric model description since they are not defined in terms of a finite number of parameters. This basic description also applies to several input signals and several output signals.

b. Parametric Models

Parameter estimation methods for linear models are based on the following procedure.

A set of candidate models must be selected, and parametrized as a model structure, using a vector $\theta$. The search for the best model within the set then becomes a problem of determining or estimating $\theta$. There are many different ways of organizing such a search and also different views on what one should search for.

Given a description (Eq. 8) and having observed the input-output data $u(t)$, $y(t)$ the predictor error $e(t)$ can be computed as:

$$e(t)=H^{-1}(q)[y(t)-G(q)u(t)] \qquad (9)$$

These errors are, for a given u and y, functions of G and H. These in turn are parametrized by polynomial or by state space matrices.

(i) Polynomial Representation

The functions G and H can be represented as a rational function of $q^{-1}$ and specify the numerator and denominator coefficients in some way. Such model structure are also known as black-box models.

A commonly used parametric model is the ARX (simple autoregressive model) that corresponds to:

$$G(q) = q^{-nk} \frac{B(q)}{A(q)}; \qquad 10.$$

$$H(q) = \frac{1}{A(q)}$$

where B and A are polynomials in the delay operator $q^{-1}$:

$$A(q)=1+a_1 q^{-1} \ldots + a_{na} q^{-na} \qquad (11)$$

$$B(q)=b_1+b_2 q^{-1} \ldots + b_{nb} q^{-nb+1} \qquad (12)$$

The numbers na and nb are the orders of the respective polynomial. The number nk is the number of delays from input to output. The model is usually written:

$$A(q)y(t)=B(q)u(t-nk)+e(t)$$

or $$y(t)+a_1 y(t-1)+ \ldots +a_{na}y(t-na)=b_1 u(t-nk)+b_2 u(t-nk-1)+ \ldots +b_{nb}u(t+nk-nb+1)+e(t) \qquad (13)$$

Eq. 13 applies also to several input signals and several output signals, where A(q) and the coefficients $a_i$ become ny×ny matrix, B(q) and the coefficients $b_i$, becomes ny×nu.

A more complex parametric model is called ARMAX model structure:

$$A(q)y(t)=B(q)u(t-nk)+C(q)e(t) C(q)=1+c_1 q^{-1}+ \ldots +c_{nc}q^{-nc} \qquad (14)$$

where A(q) and B(q) are defined in Eqs. 11 and 12.

An Output Error (OE) structure is obtained as:

$$y(t) = \frac{B(q)}{F(q)} u(t-nk) + e(t) \qquad 15.$$

with $$F(q)=1+f_1 q^{-1}+ \ldots + f_{nf} q^{-nf}$$

The so called Box-Jenkins (BJ) model structure is given by:

$$y(t) = \frac{B(q)}{F(q)} u(t-nk) + \frac{C(q)}{D(q)} e(t) \qquad 16.$$

with $$D(q)=1+d_1 q^{-1}+ \ldots + d_{nd} q^{-nd}$$

These models are special cases of the General parametric model structure:

$$A(q)y(t) = \frac{B(q)}{F(q)} u(t-nk) + \frac{C(q)}{D(q)} e(t) \qquad 17.$$

with $$F(q)=1+f_1 q^{-1}+ \ldots + f_{nf} q^{-nf}$$

and $$D(q)=1+d_1 q^{-1}+ \ldots + d_{nd} q^{-nd}$$

Within the structure of Eq. 17, virtually all of the usual linear black box model structure is obtained. For example the ARX is obtained for nc=nd=nf=0, the ARMAX is obtained for nf=nd=0.

The structures discussed may give rise to 32 ($2^5$) different model sets, depending on which of the polynomials A, B, C, D and F are used.

The same type of models can be defined for systems with an arbitrary number of inputs. They have the form:

$$A(q)y(t) = \frac{B_1(q)}{F_1(q)}u_1(t-nk_1) + \ldots + \frac{B_{nu}(q)}{F_{nu}(q)}u_{nu}(t-nk_{nu}) + \frac{C(q)}{D(q)}e(t) \qquad 18.$$

The most complete description is that of a multivariable signals where the input (u) is an m-dimensional vector and the output (y) is a p-dimensional vector. The system is still given by:

$$y(t)=G(q, 6)u(t)+H(q, 6)e(t) \qquad (19)$$

with $$G(q, 6)=A^{-1}(q)/B(q)$$

$$H(q, 6)=A^{-1}(q)$$

G(q, 6) will be p×m matrix whose entries are rational functions of $q^{-1}$.

(ii) State Space Representation

In the state space the relationship between the input, noise, and output signals is written as a system of first-order differential or difference equations using an auxiliary state vector x(t).

For the purpose of system identification it is especially useful in that insights into mechanisms of the system can usually be incorporated into state-space models than into other type of models.

The modeling usually leads to a representation:

$$u(t+1)=Ax(t)+Bu(t) \qquad (20)$$

$$y(t)=Cx(t)+Du(t)+v(t) \qquad (21)$$

Here the relationship between the input u(t) and the output y(t) is defined via the nx-dimensional state space vector x(t).

II Linear Time-varying System Identification

While linear, time-invariant models form the most common way for describing a dynamic system, it is also quiet often useful or necessary to employ other descriptions such as linear time-varying models.

A general linear system can then be described as:

$$y(t) = \sum_{k=1}^{\infty} g_t(k)u(t-k) + v(t) \qquad 22.$$

and if one writes:

$$g_t(k)=\check{g}(t,t-k) \qquad (23)$$

one finds that $$y(t) = \sum_{s=-\infty}^{t-1} \check{g}(t, s)u(s) + v(t) \qquad 24.$$

is the response at time t to a unit pulse at time s.

The function ǧ(t,s) is also known as the "weighting function", since it describes the weight that the input at time s has on the output at time t. The description in Eq. 24 is quiet analogous to the time-invariant model, except that the sequence $g_t(k)$ carries the time index t.

In general a time-varying transfer function can be introduced as:

$$G_t(q) = \sum_{k=1}^{\infty} g_t(k)q^{-k} \qquad 25.$$

and then repeat the procedures introduced above.

It is important to note that other linear system identification methods are available, such as time-varying state space model and linearization of nonlinear systems. The appropriate choice should be evaluated as a part of the identification procedure.

III. Nonlinear System Identification

A nonlinear relationship between input and output gives a rich variety of possibilities to describe the system. At the same time, the situation is far too flexible to allow for definite deduction from finite data records.

Even a first-order model without disturbances is specified only up to members in a general infinite-dimensional function space, while the corresponding linear model is characterized in terms of two real numbers.

In most cases, in order to use nonlinear models, some knowledge about the systems nonlinearities is needed in order to be able to create reasonable model structure.

The development of models for nonlinear systems is quite analogous to that described for linear systems. The basic difference is that the predictor function—which is enabling the prediction of future values—becomes a nonlinear function of past observations.

The important difference from a practical point of view is that the potential richness of possibilities makes unstructured "black-box" models unfeasible in most cases. Instead, knowledge about the character of nonlinearities will have to be built into the models. Such structure does not have to be analytical, the nonlinearities can be defined in look-up tables, and the models parameters could be entries in these tables.

There are many methods to examine nonlinear systems, methods such as NARMAX (nonlinear ARMAX) which is an extension of the commonly used parametric linear methods, up to very sophisticated nonlinear models such as Wiener results (kernels) [Wiener N: Nonlinear problems in random theory. New York Wiley; 1958] and Korenberg-Billings model [Sun H. H and Shi J. H. New algorithm for Korenberg-Billings model of nonlinear system identification. In: Advanced method of physiological system modeling: Vol II. New-York: Plenum Publishing; 1989: pp. 179–200].

The Volterra-Wiener approach is using the estimation of system kernels from input-output data. This technique employs Laguerre expansions of the kernels and estimates the unknown expansion coefficient via time-averaging of covariance samples [Marmaralis VZ: Identification of nonlinear biological systems using Laguerre expansion of kernels. Ann Biomed Eng, 21:573–589, 1993]. The Wiener kernels can also be estimated using cross correlations [Schetzen M, Lee Y W: Measurements of the Wiener kernels of nonlinear system by cross correlation: Int J control, 2: 237–254, 1965] and stochastic methods [Goussard Y. Wiener kernel estimation: A comparison of cross correlation and stochastic approximation methods. In: advanced methods of physiological system modeling: Vol I. Los Angeles, Calif.:USC Biomedical Simulations Resources; 1987: pp. 289–302].

Referring again to FIG. 6, in step 54, after deciding about the model structure, the basic model is selected out of a set of models according to a predetermined fit criterion. Assuming, for example, that the linear models family is selected, the best model in the family of linear models is picked up.

In step 56 the estimate that results from the model is evaluated. If the estimate is a good estimate according to a predetermined criterion, step 58, the identification of the connection function, is complete, is whereas if not, step 54 reexecuted and a different family of models is searched for a best model describing the dynamic system.

FIGS. 7a–c present the results of a maternal external stimulus provoked by hand grip. During hand grip, there is an increase in maternal HR (FIG. 7a), a decrease in maternal peripheral flow (PPG, FIG. 7b), and, resulting from the exercise, there is a change in fetal HR (FIG. 7c).

Following the exercise there is a fast recovery of maternal HR and flow and a slow recovery of fetal HR. This example shows that external maternal manipulation results in fetal immediate reactivity.

FIGS. 8a–c presents the result of an identification procedure on the following physiological signals: maternal HR (FIG. 8a), maternal peripheral flow (FIG. 8b) obtained by the PPG device—which is a measure of red blood cells concentration, and fetal HR (FIG. 8c). The experiment was performed on a healthy 29 years old multipara having a normal pregnancy of 26 weeks gestation.

A linear model was chosen and it was found that the best model is the Box Jenkins (BJ) model, which is a special case of the general parametric model structure shown in FIG. 8d. As shown in FIG. 8e, is the best model was achieved with the following degrees of freedom and parameters: na=2; nb=2; nc=2; nd=2; nk=1.

FIG. 8f shows the quality of this model. One way to find out the quality of a model is to simulate it and compare the model output with measured output. To this end, one selects a portion of the original data that was not used to build the model. The accuracy (or predictivity) of the model in this case was 67.8%.

When dealing with fetal HR the dynamics of the HR results from two sources: internal origin (autonomic nervous system) and external origin. The model in this case should explain the external contribution to fetal HR. Therefore, a 67.8% can be considered a very good fit.

Figure 9:
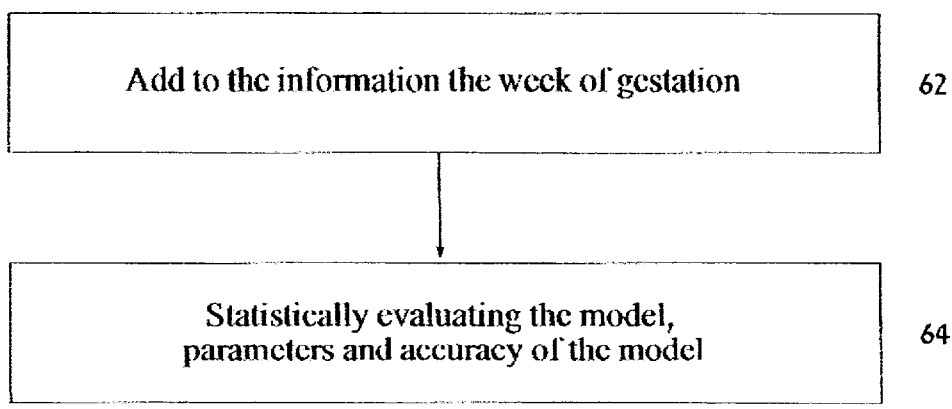
FIG. 9 is the description of the statistical procedure following the identification procedure according to the present invention.

FIG. 9 describes the statistical part of the system, step 60. In step 62 one adds to the information the week of gestation. In step 64 the results of the system identification are evaluated, taking into account the week of gestation, the family model which was used, the specific model within the model structure, the parameters of that specific model and the accuracy of the model. The conditions of the maternal-fetal unit are statistically evaluated for discriminating between high risk or low risk according to a data base previously accumulated. If further interpretation of the test such as the type of the pathology or the level of risk is available it can also be presented.

The present invention is based on the fact that the maternal-placenta-fetal dynamic system is described by open-loop models, as there is no feedback loop between the fetus and the mother.

System identification techniques, where physiological signals obtained from a specific individual in order to create a model for maternal-placenta-fetal regulation, are applied to the recorded data. The search for the appropriate model should preferably start from simple linear models and advance to more complex nonlinear models in case the linear models fail to describe the system to the extent the clinical demands require, that is that the prediction function does not permit an accurate prediction according to the rules established in the beginning of the identification procedure.

As such, system identification is a desirable tool for evaluating the effect of physiological alterations resulting from different pathologies, a change in environmental conditions and physiological stress, such as exercise.

It should be noted that a correlation between maternal pathological conditions are strongly correlated with fetus pathologies.

Pregnancies complicated by chronic hypertension are at increased risk for the development of superimposed preeclampsia, abruptio placentae, and poor prenatal outcome. As for the severity of hypertension in the first trimester, the reported incidence of superimposed preeclampsia ranges from 28.2% to 52% in severe chronic hypertension. On the other hand, the reported incidence for patients with mild hypertension in pregnancy is as low as 4.7% less.

The incidence of abruptio placenta is reportedly increased and ranges between 0.45% and 10% depending on the duration of hypertension [Sibal B M, Abdella T N, Anderson G D. Pregnancy outcome in 211 patients with mild chronic hypertension. Obstet & Gynecol 78:451, 1991].

The main risks to the fetus of the eclamptic woman are abruptio placentae, prematuity, intrauterine growth retardation.

Systemic lupus erythematosus (SLE), is a chronic disease with great diversity of clinical manifestations. SLE is associated with an increase in poor pregnancy outcome (from IUGR, stillbirth, spontaneous abortion and preterm delivery). The SLE antibodies are found in 50% of patients with SLE, and are associated with increases risk of pregnancy loss [Branch D W, Scott J R et al. Obstetrics complications associated with the lupus anticoagulant. N Eng J Med 313:1322, 1985].

During pregnancy in the insulin-dependent diabetic woman, periods of maternal hyperglycemia lead to fetal hyperinsulinemia and thus fetal pancreatic stimulation. The resulting fetal hyperinsulinemia is associated with excessive fetal growth and other morbidities. Congenital malformations are two times more common in the offspring of insulin-dependent diabetic woman. Reduced uterine blood flow is thought to contribute to the increased incidence of intrauterine growth restriction (IUGR) observed in pregnancies complicated by diabetic vasculopathy [Nyland L et al. Uteroplacental blood flow in diabetic pregnancy. Am J Obstet Gynecol 144:298, 1982].

Placenta blood flow is very sensitive to changes in maternal hemodynamic status. Administering anesthesia, either regional or general, to a parturient must involve efforts to avoid fetal compromise secondary to hypotension or intense uterine vasoconstriction. The supine position is avoided at all times, especially during anesthesia. Maternal compensation for the efforts of vena caval compression that normally occur in the absence of anesthesia can be significantly impaired when anesthesia depresses vascular reflex mechanisms. Laboring patients with epidural analgesia requiring nursing in a full or semilateral position at all times. General anesthesia is induced with the patient in a 15-degree left lateral tilt. Additionally, sudden alterations of blood pressure are avoided. Failure to treat hypotension will rapidly produce changes in the fetal heart rate tracing suggestive of hypoxia [Corke C B. Complications of obstetric anesthesia. In Francis M J (ed) Obstetric anesthesia: The complicated patient. F. A. Davis, 1990].

Thus, it is evident that maternal pathological conditions are strongly correlated with fetus pathologies, whereas the reason for that is the dynamic open loop system characterizing the maternal-placenta-fetus.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLE

Reference is now made to the following example, which together with the above descriptions, illustrate the invention in a non limiting fashion.

Theoretical Model

Figure 10:
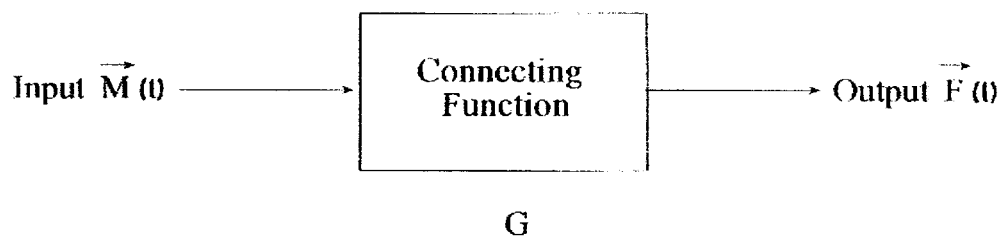
FIG. 10 illustrates a theoretical model according to the present invention. The physiological state of the fetus, represented by a vector of physiological parameters $\vec{F}(t)$ is related to the physiological state of the mother, again represented by a vector $\vec{M}(t)$, through a connecting function G. This theoretical model is not technically feasible.

A theoretical model for the mother-placenta-fetus system as is illustrated in FIG. 10, shall be considered first. As shown in FIG. 10, a vector containing all physiological parameters of the mother represents the physiological state of the mother. The time evolution of this vector is highly complicated, as is human physiology. The value of the vector (denoted by $\vec{M}(t)$) at any instant t is determined by the following factors: (i) past values of this vector; (ii) the emotional state of the mother; and (iii) the coupling to the outside world.

The maternal physiology is represented by first kind of influences. An example of such influences, is the increase in heart rate in response to a decrease in blood pressure. The second kind of influences represents the effect of emotions on the body. Such influences are exemplified by the increase in heart rate in response to emotional stress. The third kind of influences represents the response of the maternal body to the outside world (e.g., the response of the body to a change in external temperature).

In the same manner, the physiological state of the fetus is represented by a vector of all its physiological parameters, $\vec{F}(t)$. The fetus is coupled to his mother mainly through the placenta. The fetus is also coupled to his mother through a mechanical coupling. The mechanical coupling is exemplified by influence of uterine contraction on fetal heart rate. The outside world has little direct effect on the fetus, since all outside influences are mediated through the mother. Therefore, the physiological state of fetus at any instant t, which is represented by $\vec{F}(t)$, is determined by: (i) past values of $\vec{F}(t)$; (ii) the physiological state of the mother $\vec{M}(t)$; (iii) the coupling between the mother and the fetus; and (iv) the emotional state of the fetus.

The fetus-mother system is therefore modeled by the following equation:

$$\vec{F}(t) = \hat{G}_{\tau,\nu\leq t}\left(\vec{F}(\tau), \vec{M}(\nu)\right) + \vec{N}(t) \qquad 26.$$

G is the functional relation between the current state of the fetus and previous states of both the mother and the fetus himself. The vector $\vec{N}(t)$ represents the contribution from factors, which are independent of the physiology of both mother and fetus. The function G represents the coupling and influence of the mother on the fetus. An accurate estimate of G would enable to determine the health of the placenta. In reality, it is technically impossible to determine $\vec{M}(t)$ nor $\vec{F}(t)$ and therefore it is also impossible to estimate G. However, there are physiological signals which are technically measurable, that enable to construct a model of the system.

Realistic Complex Model

Figure 11:
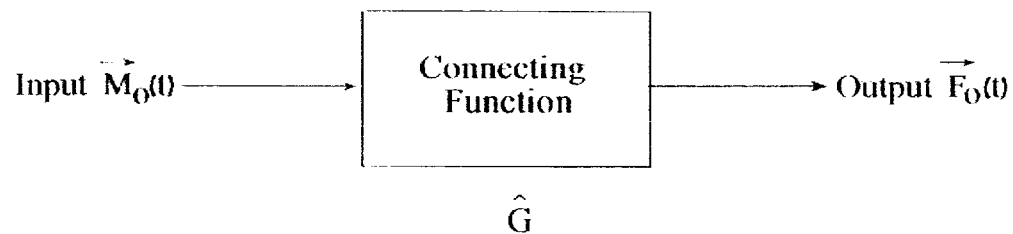
FIG. 11 illustrates a realistic complex model according to the present invention. A vector of observed physiological signals, $\vec{F}_O(t)$, represents the physiological state of the fetus. The dimension of $\vec{F}_O(t)$ is finite and much lower than that of $\vec{F}(t)$. In the same manner, a vector $\vec{M}_O(t)$, which represents the physiological state of the mother, is constructed. The dimension of $\vec{M}_O(t)$ is larger than that of $\vec{F}_O(t)$ since more maternal physiological signals can be measured. Estimation of the connecting function of the two systems ($\hat{G}$) is possible.

FIG. 11 describes a method to obtain a realistic model of the mother-fetus interaction while maintaining the accuracy of the complex model. A model of the mother-fetus interaction can be built using measurable physiological signals of both mother and fetus. These signals are highly correlated with the relevant physiological state of the mother and fetus. The mathematical formulation of the model is shown in the following equation:

$$\vec{F}_O(t) = \hat{G}_{\tau,\nu\leq t}\left(\vec{F}_O(\tau), \vec{M}_O(\nu)\right) + \vec{N}'(t) \qquad 27.$$

where $\vec{F}_O(t)$ is a vector of the observed physiological signals, obtained from the fetus, and $\vec{M}_O(t)$ is the vector of observed physiological signals obtained from the mother. $\hat{G}$ is the connecting function which relates the two systems (mother and fetus), $\vec{N}'(t)$ is the part of the fetus' physiology which is independent from the mother and from past values of $\vec{F}_O(t)$ and is regarded according to the realistic model as noise. The dimensions of $\vec{F}_O(t)$, $\vec{M}_O(t)$ and $\vec{N}'(t)$ is much smaller than the number of elements of $\vec{F}(t)$ $\vec{M}(t)$ and $\vec{N}(t)$. As a result, it is a technically feasible to assess the function $\hat{G}$ from measurable signals.

Signals Selection

There are several considerations in selecting the signals from which the model is built. The first consideration is the ease of obtaining the signals. Signals that can be acquired noninvasively are preferred. However, invasive measurements are sometimes adequate (especially when the subject already undergoes an invasive testing procedure). Noise free signals are also preferred. The next consideration is the extent of physiological information embedded in the signal. Signals which reflect important physiological parameters, such as the blood pressure are preferred. The last consideration is the cross-correlation between the signals. It is best to avoid the recording of signals which represent the same physiological parameter or add little information to the model. Note that this consideration should not be interpreted in a linear sense. The shared information between two signals is not always characterized by linear correlation [H. D. I. Abarbanel, Analysis of observed chaotic data, Springer-Verlag 1996].

The Acquired Signals

The vector $\vec{F}_O(t)$ is composed from some or all of the following signals: Doppler signal from an ultrasound transducer, directed to the fetal heart; Doppler signal from an ultrasound transducer, directed to the umbilical cord; ECG signal; other signals can also be included.

The vector $\vec{M}_O(t)$ is composed of some or all of the following signals: ECG; photoplethysmograph; respiration; uterine activity; oxygen saturation; $CO_2$ saturation; Other signals can also be utilized.

The connecting function $\hat{G}$ between the two systems is complex, since the measurable signals are related to the basic physiological parameters of both mother and fetus in a complex and nonlinear way.

In order to overcome this obstacle, one applies a nonlinear transformation to both the $\vec{F}_O(t)$ and $\vec{M}_O(t)$, thus changing the connecting function $\hat{G}$ to a simpler function.

A Simplified Model

Figure 12:
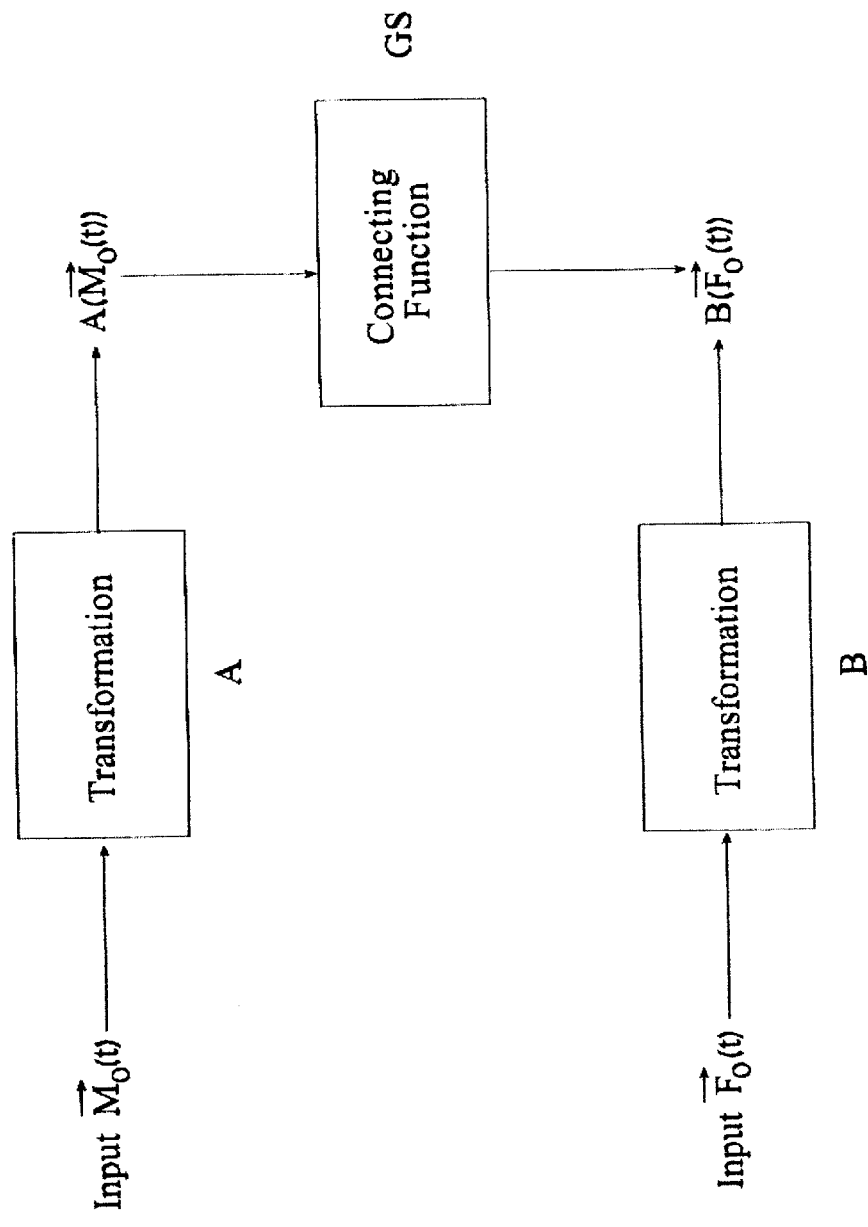
FIG. 12 illustrates a realistic simple model according to the present invention. The transformations A and B transform the vectors $\vec{M}_O(t)$ and $\vec{F}_O(t)$. The connecting function between the transformed vectors ($G_S$) is much simpler than $\hat{G}$. The nature of the transformations is determined by knowledge of the underlying physiology.
Figure 16:
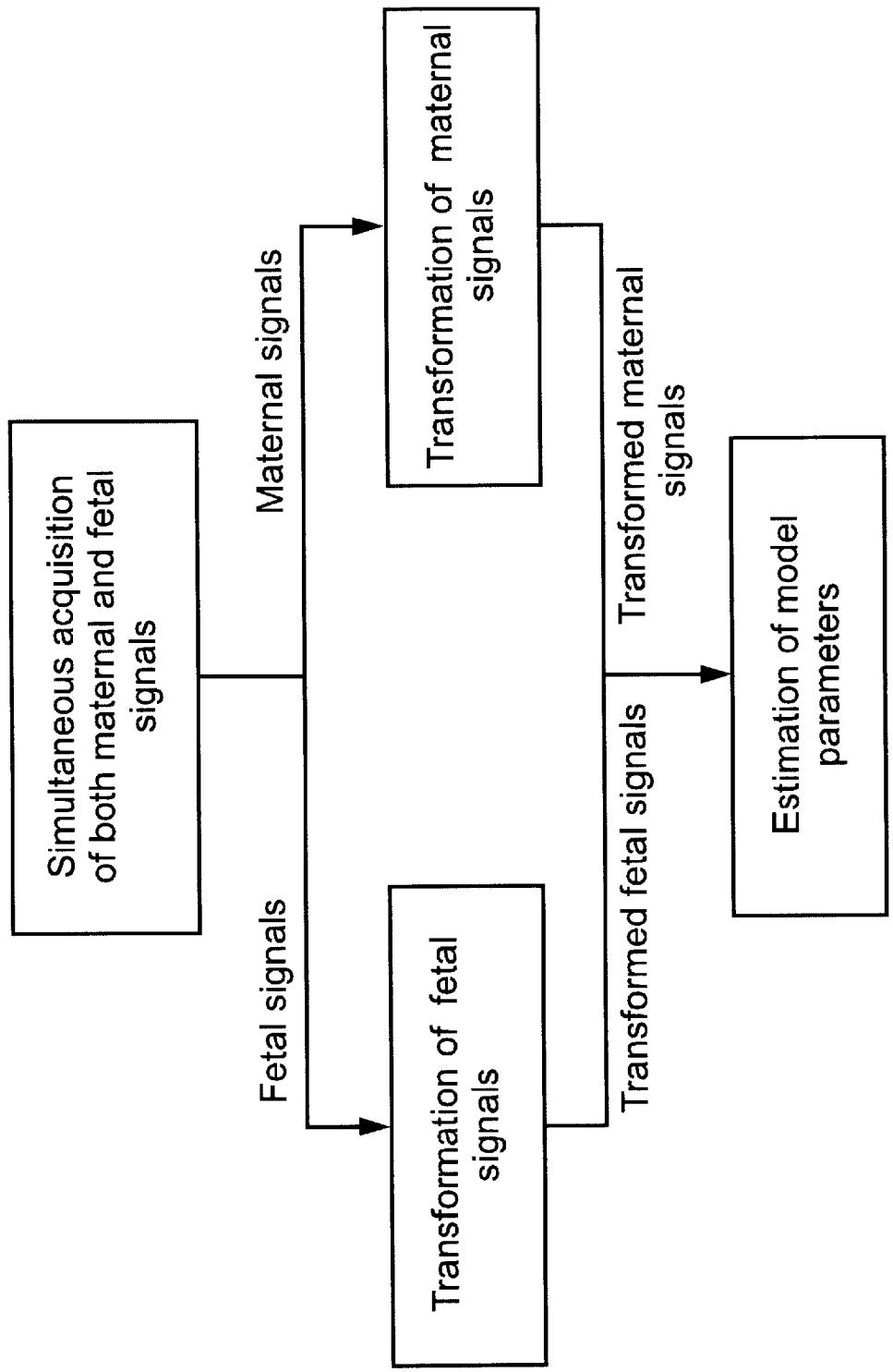
FIG. 16 is a flow diagram showing the flow of data in a medical system according to the present invention.

As shown in FIGS. 12 and 16, in order to simplify the connecting function, it is decomposed into three parts. First transformation A (denoted A) is applied on the input maternal vector $\vec{M}_O(t)$. The result of transformation A is $\vec{M}_T(t)$. Then, transformation B (denoted B) is applied on the fetal input vector $\vec{F}_O(t)$. The result of transformation B is $\vec{F}_T(t)$. Note that the dimension of the transformed vectors are higher or equal to that of the original vectors. The connecting function $\hat{G}$ changes to $G_S$. Suitable transformations A and B enable to obtain a connecting function $G_S$ which is much simpler than $\hat{G}$. The key to the construction of simplifying transformations is the knowledge of the physiology of the systems. The transformations extract the physiological information, which exists implicitly in the acquired signals. The generated signals, known also as pseudo-signals, correlate with basic physiological parameters of the mother and fetus. For example, the heart rate pseudo-signal is related to the cardiac output linearly, whereas the ECG has complicated, nonlinear correlation with the cardiac output. The connecting function between the basic physiological parameters is much simpler than the connecting function between the measured signals. Therefore, the transformations of the measured signals enable to find a simple connecting function between the measured signals. The simple connecting function could be assessed by a linear model, or almost linear model. An example of such transformation is the transition from the ECG trace to heart rate. The ECG trace incorporates all information regarding the heart rate but an attempt to find the connecting function between the maternal ECG and fetal physiological state is difficult. In order to simplify the mathematical relation between the ECG and fetal state, one extracts the physiological information, which underlies the ECG. Other transformations could be applied to ECG recordings in order to extract other physiological information. Moreover, the transformation could transform more than one input signal into a single io output signal.

The transformation of each signal of the mother and fetus is different.

The following lists some of the transformations which can be used:

1. Maternal ECG—the R waves of the maternal ECG are detected. The time of the k'th R wave is represented by $t_k$. The maternal heart rate is calculated from the inter-beat interval: HR=

$$HR = \frac{60}{t_{k+1} - t_k}.$$

The units are Beats Per Minute (BPM). This transformation is similar to the known Pulse Position Modulation [Couch L. W. Digital and Analog Communication Systems. 5th ed., 1997 Prenctice-Hall Jew-Jersey]

Figure 13:
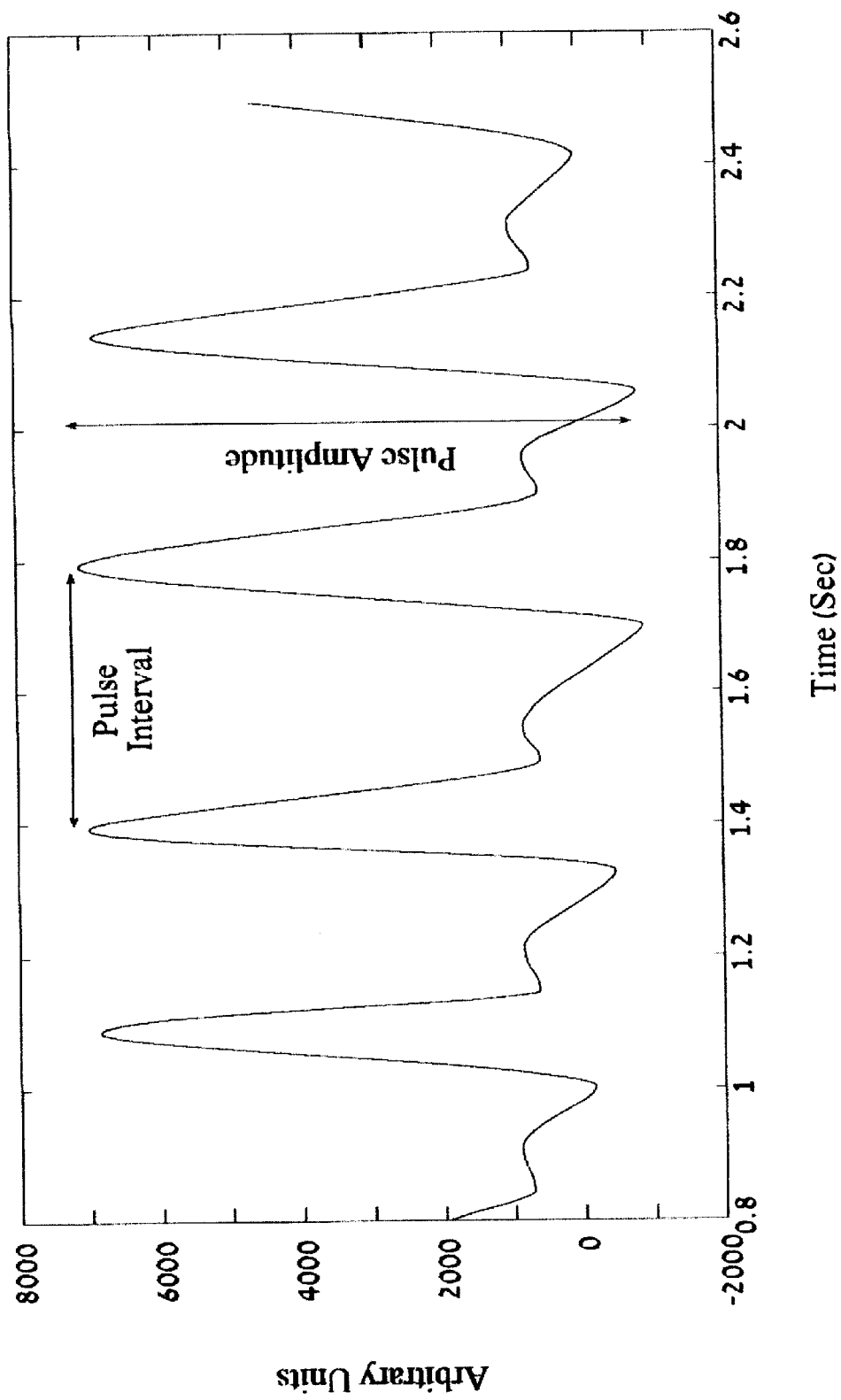
FIG. 13 shows the definitions of the Pulse Interval and Pulse Amplitude of a PPG signal.
Figure 14:
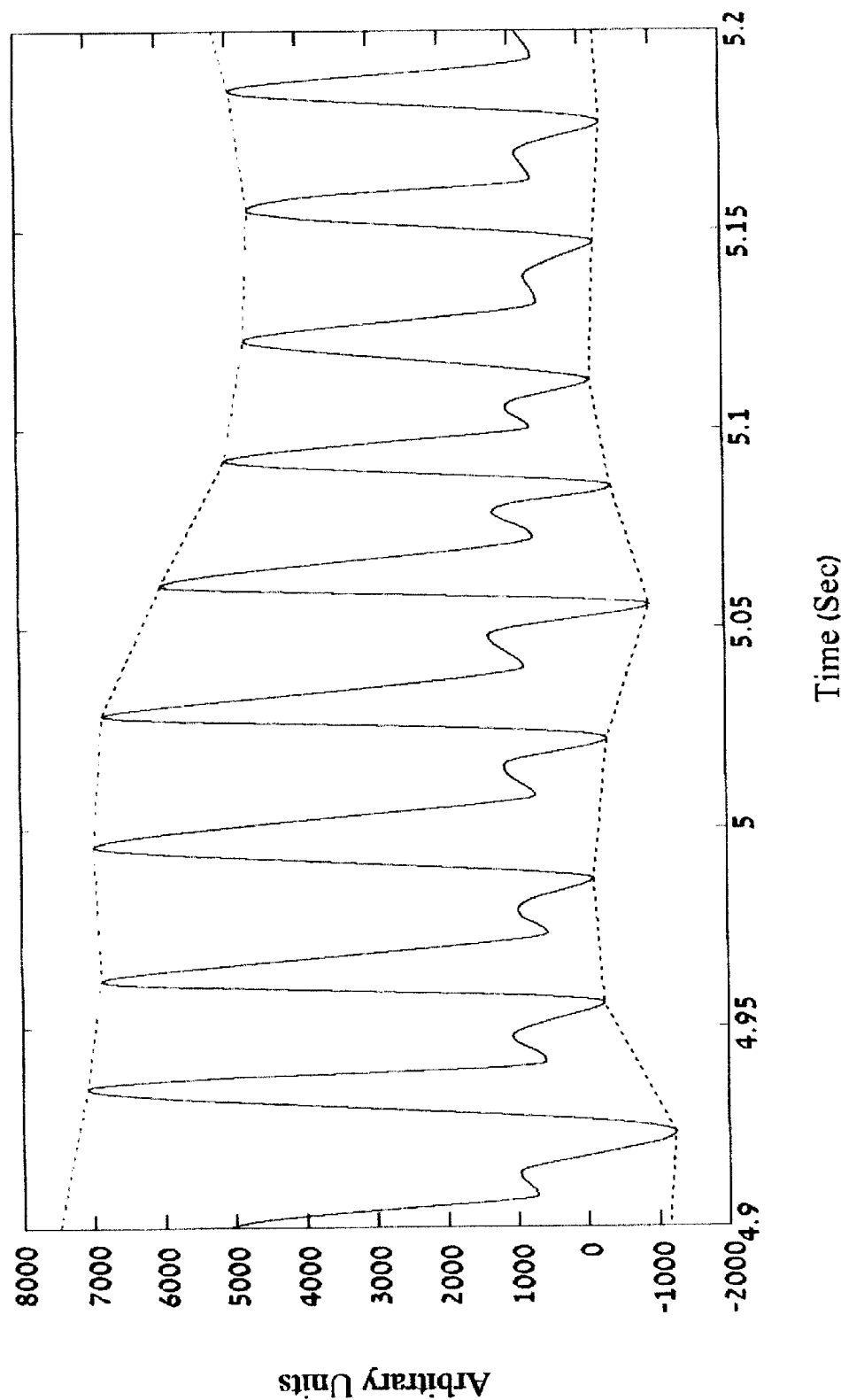
FIG. 14 shows the result of extraction of the pulse amplitude from the PPG signal of FIG. 13.

2. Maternal PPG—As shown in FIGS. 13–14, the maxima of the signals are detected. The maternal heart rate is calculated from the inter-beat intervals, similarly to the calculation of the heart rate from ECG.

3. Maternal PPG—The amplitude of the signals are calculated. This transformation is actually demodulating the PPG signal using a DSB-SC scheme. The signal of the amplitude is low-pass filtered (fc=40 Hz) in order to reduce noise. This signal is a measure of the amount of blood in the tissue, and therefore correlates with peripheral blood flow.

4. Fetal ECG—The fetal heart rate is calculated in the same way as the maternal heart rate.

5. Doppler signal from ultrasound signal of the fetal heart—valve closing is detected and fetal heart rate is calculated from the inter-beat interval.

6. Ultrasound reflection from a fetal blood vessel—the reflected signal is FM demodulated in order to extract the Doppler shift due to blood flow in the reflecting tissue. The blood flow is calculated from the amplitude of the Doppler signal (DSB-SC demodulation).

7. Ultrasound reflection from a fetal blood vessel—the reflected signal is FM demodulated in order to extract the Doppler shift due to blood flow in the reflecting tissue. The intervals between consecutive systoles are calculated. Fetal heart rate is calculated from these intervals.

8. Ultrasound reflection from a fetal blood vessel—FM demodulation of the reflected ultrasound signal provides a measure of the velocity of the blood, due to the Doppler effect.

Figure 15:
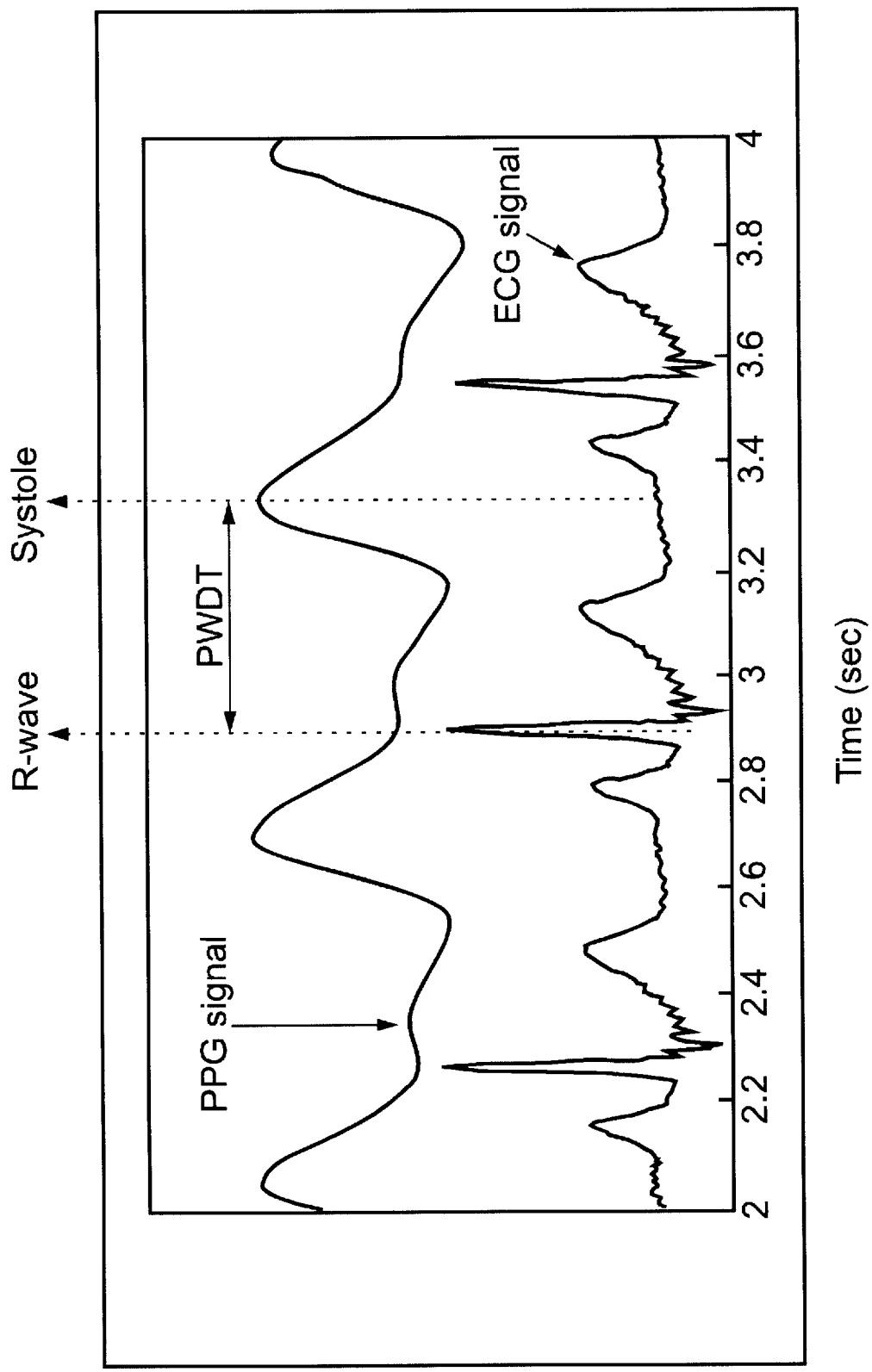
FIG. 15 shows the extraction of the delay between the R-wave obtained from an ECG and the systole, obtained form a simultaneously measured PPG signal.

9. ECG and Maternal PPG—the delays between the R-waves (of the ECG) and the corresponding systoles (in the PPG signal) are calculated (see FIG. 15). This delay includes the blood pressure wave transmission time from the aorta to the peripheral blood vessel and the pre-ejection period of the heart. This measure is closely related to the pulse wave velocity, and therefore to blood pressure [Zong W., Moody G. B., Mark R. G., Effects of vasoactive drugs on the relationship between ECG-pulse wave delay time and arterial blood pressure in ICU patients. Comp. In Card. 1998;25, 673–676; Gosse P., Guillo P., Ascher G., Clementy J. Assessment of Arterial distensibility by monitoring the timing of Korotkoff sounds. Am J Hypertension 1994;7, 228–233; Hasegawa M., Nagao K., Kinoshita Y., Rodbard D., Asahina A. Increased pulse wave velocity and shortened pulse wave transmission time in hypertension and aging. Cardiology 1997; 88, 147–151].

10. Maternal PPG—maximal derivative in the systole stage is calculated. The maximal derivative is related to maternal contractility. It is therefore also indirectly linked to sympathetic activation to the heart.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications cited herein are incorporated by reference in their entirety.

What is claimed is:

1. A method of determining the well being of a placenta in a pregnant woman having a maternal-placenta-fetal system, the method comprising the steps of:

(a) simultaneously monitoring selected maternal and fetal physiological signals;

(b) preprocessing said maternal and fetal physiological signals by independently non-linearly or linearly mathematically decomposing said maternal and fetal physiological signals into mathematical constituents thereof and collecting constituents of said mathematical constituents having a highest degree of linearity and/or simplicity;

(c) using said constituents having said highest degree of linearity and/or simplicity for identifying a mathematical model describing the maternal-placenta-fetal system, and mathematical parameters describing said model; and (d) determining, according to said mathematical model and said mathematical parameters describing said mathematical model, the well being of the placenta.

2. The method of claim 1, wherein while simultaneously monitoring said selected maternal and fetal physiological signals the pregnant woman is provoked by an external stimulus.

3. The method of claim 1, wherein said physiological signals are selected from the group consisting of ECG, BP, $PO_2$, $PCO_2$, blood flow, blood velocity, blood volume, thermal index and respiration.

4. The method of claim 1, wherein said mathematical model is selected from the group consisting of nonparametric models, parametric models, polynominal representation, simple autoregressive model, ARMAX model structure, output error structure, Box-Jenkins model structure, general parametric model structure, state space representation, linear time-varying models, time-invariant model, nonlinear models, nonlinear ARMAX, Wiener kernels model, Korenberg-Billings model and Volterra-Wiener model.

5. The method of claim 1, wherein said step of identifying said mathematical model is effected by identifying a best mathematical model describing the maternal-placenta-fetal system, said best mathematical model is selected out of a plurality of available mathematical models and according to predetermined criteria.

6. The method of claim 1, wherein said model is a linear model.

7. The method of claim 1, wherein said step of preprocessing said maternal and fetal physiological signals includes at least one process selected from the group consisting of:
  (i) calculating a maternal heart rate from an inter-beat interval of maternal ECG;
  (ii) calculating maternal heart rate from maxima values of maternal blood flow;
  (iii) calculating a maternal pulse wave velocity from a delay between R-waves of an ECG and corresponding systoles of blood flow signal;
  (iv) calculating maternal contractility from maternal blood flow by determining maximal derivative in a maternal systole stage;
  (v) calculating a fetal heart rate from an inter-beat interval of fetal ECG;
  (vi) calculating a fetal heart rate from an inter-beat interval of fetal Doppler signal representing fetal heart valve closing;
  (vii) calculating a fetal blood flow using ultrasound reflection from a fetal blood vessel; and
  (viii) calculating a fetal heart rate from fetal blood flow rate; and
  (ix) calculating a fetal blood flow rate using ultrasound reflection from a fetal blood vessel.

8. A method of determining the well being of a fetus in a pregnant woman having a maternal-placenta-fetal system, the method comprising the steps of:
  (a) simultaneously monitoring selected maternal and fetal physiological signals;
  (b) preprocessing said maternal and fetal physiological signals by independently non-linearly or linearly mathematically decomposing said maternal and fetal physiological signals into mathematical constituents thereof and collecting constituents of said mathematical constituents having a highest degree of linearity and/or simplicity;
  (c) using said constituents having said highest degree of linearity and/or simplicity for identifying a mathematical model describing the maternal-placenta-fetal system, and mathematical parameters describing said model; and
  (d) determining, according to said mathematical model and said mathematical parameters describing said mathematical model, the well being of the fetus.

9. The method of claim 8, wherein while simultaneously monitoring said selected maternal and fetal physiological signals the pregnant woman is provoked by an external stimulus.

10. The method of claim 8, wherein said physiological signals are selected from the group consisting of ECG, BP, $PO_2$, $PCO_2$, blood flow, blood velocity, blood volume, thermal index and respiration.

11. The method of claim 8, wherein said mathematical model is selected from the group consisting of nonparametric models, parametric models, polynominal representation, simple autoregressive model, ARMAX model structure, output error structure, Box-Jenkins model structure, general parametric model structure, state space representation, linear time-varying models, time-invariant model, nonlinear models, nonlinear ARMAX, Wiener kernels model, Korenberg-Billings model and Volterra-Wiener model.

12. The method of claim 8, wherein said step of identifying said mathematical model is effected by identifying a best mathematical model describing the maternal-placenta-fetal system, said best mathematical model is selected out of a plurality of available mathematical models and according to predetermined criteria.

13. The method of claim 8, wherein said model is a linear model.

14. The method of claim 8, wherein said step of preprocessing said maternal and fetal physiological signals includes at least one process selected from the group consisting of:
  (i) calculating a maternal heart rate from an inter-beat interval of maternal ECG;
  (ii) calculating maternal heart rate from maxima values of maternal blood flow;
  (iii) calculating a maternal pulse wave velocity from a delay between R-waves of an ECG and corresponding systoles of blood flow signal;
  (iv) calculating maternal contractility from maternal blood flow by determining maximal derivative in a maternal systole stage;
  (v) calculating a fetal heart rate from an inter-beat interval of fetal ECG;
  (vi) calculating a fetal heart rate from an inter-beat interval of fetal Doppler signal representing fetal heart valve closing;
  (vii) calculating a fetal blood flow using ultrasound reflection from a fetal blood vessel; and
  (viii) calculating a fetal heart rate from fetal blood flow rate; and
  (ix) calculating a fetal blood flow rate using ultrasound reflection from a fetal blood vessel.

15. A method of determining a maternal-fetus relation in a pregnant woman having a maternal-placenta-fetal system, the method comprising the steps of:
  (a) simultaneously monitoring selected maternal and fetal physiological signals;
  (b) preprocessing said maternal and fetal physiological signals by independently non-linearly or linearly mathematically decomposing said maternal and fetal physiological signals into mathematical constituents thereof and collecting constituents of said mathematical constituents having a highest degree of linearity and/or simplicity;

(c) using said constituents having said highest degree of linearity and/or simplicity for identifying a mathematical model describing the maternal-placenta-fetal system, and mathematical parameters describing said model; and (d) determining, according to said mathematical model and said mathematical parameters describing said mathematical model, the maternal-fetus relation.

16. The method of claim 15, wherein while simultaneously monitoring said selected maternal and fetal physiological signals the pregnant woman is provoked by an external stimulus.

17. The method of claim 15, wherein said physiological signals are selected from the group consisting of ECG, BP, $PO_2$, $PCO_2$, blood flow, blood velocity, blood volume, thermal index and respiration.

18. The method of claim 15, wherein said mathematical model is selected from the group consisting of nonparametric models, parametric models, polynominal representation, simple autoregressive model, ARMAX model structure, output error structure, Box-Jenkins model structure, general parametric model structure, state space representation, linear time-varying models, time-invariant model, nonlinear models, nonlinear ARMAX, Wiener kernels model, Korenberg-Billings model and Volterra-Wiener model.

19. The method of claim 15, wherein said step of identifying said mathematical model is effected by identifying a best mathematical model describing the maternal-placenta-fetal system, said best mathematical model is selected out of a plurality of available mathematical models and according to predetermined criteria.

20. The method of claim 15, wherein said model is a linear model.

21. The method of claim 15, wherein said step of preprocessing said maternal and fetal physiological signals includes at least one process selected from the group consisting of:

(i) calculating a maternal heart rate from an inter-beat interval of maternal ECG;

(ii) calculating maternal heart rate from maxima values of maternal blood flow;

(iii) calculating a maternal pulse wave velocity from a delay between R-waves of an ECG and corresponding systoles of blood flow signal;

(iv) calculating maternal contractility from maternal blood flow by determining maximal derivative in a maternal systole stage;

(v) calculating a fetal heart rate from an inter-beat interval of fetal ECG;

(vi) calculating a fetal heart rate from an inter-beat interval of fetal Doppler signal representing fetal heart valve closing;

(vii) calculating a fetal blood flow using ultrasound reflection from a fetal blood vessel; and (viii) calculating a fetal heart rate from fetal blood flow rate; and (ix) calculating a fetal blood flow rate using ultrasound reflection from a fetal blood vessel.

22. A system for monitoring a pregnancy in a pregnant woman having a maternal-placenta-fetal system, the system comprising:

(a) at least one monitoring device simultaneously monitoring selected maternal and fetal physiological signals; and (b) a computerized system being in communication with each of said at least one monitoring device for preprocessing said maternal and fetal physiological signals by independently non-linearly or linearly mathematically decomposing said maternal and fetal physiological signals into mathematical constituents thereof and collecting constituents of said mathematical constituents having a highest degree of linearity and/or simplicity, and for using said constituents having said highest degree of linearity and/or simplicity for identifying a mathematical model describing the maternal-placenta-fetal system, and mathematical parameters describing said model.

23. The system of claim 22, wherein said physiological signals are selected from the group consisting of ECG, BP, $PO_2$, $PCO_2$, blood flow, blood velocity, blood volume, thermal index and respiration.

24. The system of claim 22, wherein said mathematical model is selected from the group consisting of nonparametric models, parametric models, polynominal representation, simple autoregressive model, ARMAX model structure, output error structure, Box-Jenkins model structure, general parametric model structure, state space representation, linear time-varying models, time-invariant model, nonlinear models, nonlinear ARMAX, Wiener kernels model, Korenberg-Billings model and Volterra-Wiener model.

25. The system of claim 22, wherein identifying said mathematical model is effected by identifying a best mathematical model describing the maternal-placenta-fetal system, said best mathematical model is selected out of a plurality of available mathematical models and according to predetermined criteria.

26. The system of claim 22, wherein said model is a linear model.

27. The system of claim 22, wherein preprocessing said maternal and fetal physiological signals includes at least one process selected from the group consisting of:

(i) calculating a maternal heart rate from an inter-beat interval of maternal ECG;

(ii) calculating maternal heart rate from maxima values of maternal blood flow;

(iii) calculating a maternal pulse wave velocity from a delay between R-waves of an ECG and corresponding systoles of blood flow signal;

(iv) calculating maternal contractility from maternal blood flow by determining maximal derivative in a maternal systole stage;

(v) calculating a fetal heart rate from an inter-beat interval of fetal ECG;

(vi) calculating a fetal heart rate from an inter-beat interval of fetal Doppler signal representing fetal heart valve closing;

(vii) calculating a fetal blood flow using ultrasound reflection from a fetal blood vessel; and (viii) calculating a fetal heart rate from fetal blood flow rate; and (ix) calculating a fetal blood flow rate using ultrasound reflection from a fetal blood vessel.

* * * * *